United States Patent [19]
Fujita et al.

[11] Patent Number: 5,436,257
[45] Date of Patent: Jul. 25, 1995

[54] OXAZOLIDINE DERIVATIVES HAVING ANTI-DIABETIC AND ANTI-OBESITY PROPERTIES, THEIR PREPARATION AND THEIR THERAPEUTIC USES

[75] Inventors: Takashi Fujita; Takao Yoshioka; Shinji Yoshioka; Toshihiko Fujiwara; Hiroyoshi Horikoshi, all of Tokyo, Japan

[73] Assignee: Sankyo Company, Limited, Tokyo, Japan

[21] Appl. No.: 114,006

[22] Filed: Aug. 30, 1993

[30] Foreign Application Priority Data

Aug. 31, 1992 [JP] Japan .................... 4-231140

[51] Int. Cl.$^6$ .............. C07D 417/12; A61K 31/425
[52] U.S. Cl. ........................... 514/369; 548/183
[58] Field of Search ................... 548/183; 514/369

[56] References Cited

U.S. PATENT DOCUMENTS 4,572,912  2/1986  Yoshioka et al. .............. 514/369
4,968,707  11/1990  Clark ........................... 514/340

FOREIGN PATENT DOCUMENTS 0008203  2/1980  European Pat. Off. .
0139421  5/1985  European Pat. Off. .
0441605  8/1991  European Pat. Off. .
9207838  5/1992  WIPO .......................... 548/183

OTHER PUBLICATIONS

N. Engl. J. Med., 317, 350–357 (1987).
Diabetes, 37, 1595–1607 (1988).
Diabetes, 39, 477–482 (1990).
Endocrinology, 119, 1786–1792 (1986).
Chem. Pharm. Bull., 30, 3580–3600 (1982).

*Primary Examiner*—Robert Gerstl
*Attorney, Agent, or Firm*—Frishauf, Holtz, Goodman & Woodward

[57] ABSTRACT

Compounds of formula (I):

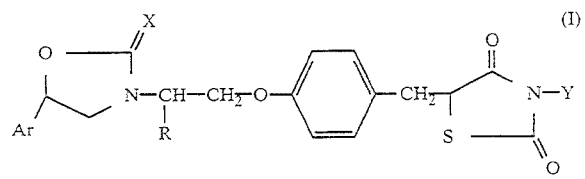

wherein: R is an alkyl group; X is oxygen or sulfur; Y is hydrogen atom or —A—COOH, in which A is an alkylene group; Ar is aryl or substituted aryl group; and pharmaceutically acceptable salts and esters thereof, have use in the treatment or prophylaxis of diabetes, obesity, hyperlipemia, hyperglycemia, complications of diabetes, obesity-related hypertension and osteoporosis.

34 Claims, No Drawings

OXAZOLIDINE DERIVATIVES HAVING ANTI-DIABETIC AND ANTI-OBESITY PROPERTIES, THEIR PREPARATION AND THEIR THERAPEUTIC USES

BACKGROUND TO THE INVENTION

The present invention relates to a series of new oxazolidine derivatives, which exhibit valuable anti-diabetic and anti-obesity activities, rendering the compounds suitable for use in the treatment or prevention of hyperlipemia and hyperglycemia, and, by inhibiting the action of aldose reductase, they can also be effective in the treatment and prevention of complications of diabetes. They are also effective in the treatment and prophylaxis of obesity-related hypertension and osteoporosis. The invention also provides processes for preparing the compounds of the present invention, as well as methods and compositions using them.

Thiazolidine derivatives, which are structurally related to the compounds of the present invention and are active in reducing blood sugar levels are known and are described in, for example, Japanese Patent Application Kokai No. Sho 55-22636 (Tokko No. Sho 62-42903); Japanese Patent Application Kokai No. Sho 60-51189 (Tokko No. Hei 2-31079); Kawamatsu et al., Chem. Pharm. Bull., 30, (1982) 3580-3600 and European Patent Publication No. 441,605.

European Patent Publication No. 294,995 and PCT WO 92/07838, which are currently thought to represent the closest prior art, disclose compounds which are structurally similar to those of the present invention. The compounds from these two prior art documents which are believed to be structurally the closest to the compounds of the present invention are represented by formula (M) and formula (N), below. The compound of formula (M), which is 3-{2-[4-(2,4-dioxothiazolidin-5-ylmethyl)phenyl]-1-methylethyl}-5-(3-chlorophenyl)oxazolidin-2-one, is described in European Patent Publication No. 294,995, and the compound of formula (N), which is 3-{2-[4-(2,4-dioxothiazolidin-5-ylmethyl)phenoxy]ethyl}-5-phenyloxazolidin-2-one, is described in PCT WO 92/07838.

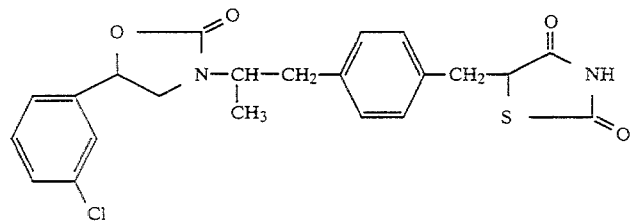

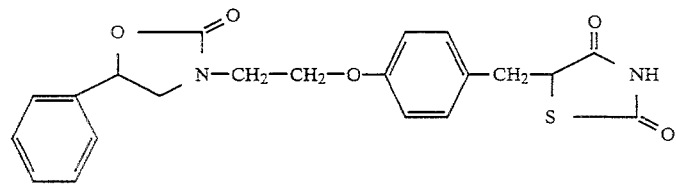

The compounds of the prior art do, however, have limited activity. There is therefore still a need for compounds with improved activity and toxicity characteristics.

We have now discovered a limited series of novel oxazolidine derivatives which have valuable anti-diabetic and anti-obesity activities, as well as being suitable for treating conditions associated with obesity and diabetes, and which have a low toxicity.

BRIEF SUMMARY OF THE INVENTION

It is, therefore, an object of the present invention to provide a series of compounds of this type.

It is a further, and more specific, object of the invention to provide such compounds having anti-diabetic and anti-obesity activities, and preferably having a low toxicity.

It is a further object of the invention to provide methods and compositions using these compounds.

Other objects and advantages will become apparent as the description proceeds.

The compounds of the present invention are those compounds of formula (I):

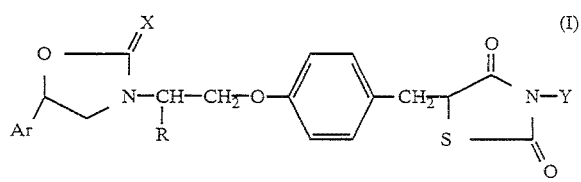

wherein:
- R represents an alkyl group having from 1 to 8 carbon atoms;
- X represents an oxygen atom or a sulfur atom;
- Y represents a hydrogen atom or a group of formula —A—COOH, in which A represents an alkylene group having from 1 to 6 carbon atoms;
- Ar represents an unsubstituted aryl group having from 6 to 10 ring carbon atoms or a substituted aryl group which has from 6 to 10 carbon atoms and which is substituted by at least one substituent selected from the group consisting of substituents (a);
- said substituents (a) are selected from the group consisting of: halogen atoms; haloalkyl groups, in which the alkyl part has from 1 to 4 carbon atoms; hydroxy groups; alkyl groups having from 1 to 4 carbon atoms; and alkoxy groups having from 1 to 4 carbon atoms;

and pharmaceutically acceptable salts and esters thereof.

The invention also provides a pharmaceutical composition for the treatment or prophylaxis of diabetes, obesity, hyperlipemia, hyperglycemia, complications of diabetes, obesity-related hypertension and osteoporosis, which composition comprises an effective amount of an active compound in admixture with a pharmaceutically acceptable carrier or diluent, wherein the active compound is selected from the group consisting of compounds of formula (I) and pharmaceutically acceptable salts and esters thereof.

The invention also provides a method for the treatment or prophylaxis of diabetes, obesity, hyperlipemia, hyperglycemia, complications of diabetes, obesity-related hypertension and osteoporosis in a mammal, which may be human, which method comprises administering to said mammal an effective amount of an active compound, wherein the active compound is selected from the group consisting of compounds of formula (I) and pharmaceutically acceptable salts and esters thereof.

The invention also provides processes for preparing the compounds of the present invention, which are described in more detail hereafter.

DETAILED DESCRIPTION OF THE INVENTION

In the compounds of this invention, where R represents an alkyl group, this may be a straight or branched chain alkyl group having from 1 to 8 carbon atoms. Examples of such alkyl groups include the methyl, ethyl, propyl, isopropyl, butyl, isobutyl, sec-butyl, t-butyl, pentyl, 2-pentyl, 3-pentyl, 2-methylbutyl, 3-methylbutyl, 1,1-dimethylpropyl, 1,2-dimethylpropyl, 2,2-dimethylpropyl, hexyl, 2-hexyl, 3-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, heptyl, 2-heptyl, 3-heptyl, 4-heptyl, 3,3-dimethylpentyl, octyl, 1-methylheptyl, 2-ethylhexyl and 1,1,3,3-tetramethylbutyl groups. When R represents an alkyl group, this is preferably a straight or branched chain alkyl group having from 1 to 6 carbon atoms, and most preferably, this is a straight or branched chain alkyl group having from 1 to 4 carbon atoms, particularly the methyl or ethyl group.

Where A represents an alkylene group, this may be straight or branched chain alkylene group having from 1 to 6 carbon atoms, and preferably from 1 to 4 carbon atoms. Examples of such alkylene groups include: the methylene, ethylene, ethylidene, trimethylene, propylidene, 1-methylethylene, 2-methylethylene, tetramethylene, 1-methyltrimethylene, 2-methyltrimethylene, 3-methyltrimethylene, isopropylidene, 1,2-dimethylethylene, 1-ethylethylene, 2-ethylethylene, pentamethylene, 1-methyltetramethylene, 2-methyltetramethylene, 1,2-dimethyltrimethylene, 1,3-dimethyltrimethylene, 2,2-dimethyltrimethylene, 1-methyl-2-ethylethylene, 1,2,2-trimethylethylene, 1-propylethylene, hexamethylene, 1-methylpentamethylene, 2-methylpentamethylene, 3-methylpentamethylene, 5-methylpentamethylene, 1,2-dimethyltetramethylene, 1,3-dimethyltetramethylene, 1,4-dimethyltetramethylene, 1-ethyltetramethylene, 2-ethyltetramethylene, 1-methyl-2-ethyltrimethylene, 2-methyl-2-ethyltrimethylene, 2-propyltrimethylene, 1,1-diethylethylene, 1,2-diethylethylene or 1-methyl-2-propylethylene groups.

Where Ar represents an aryl group having from 6 to 10 carbon atoms, this is preferably an aryl group having from 6 or 10 carbon atoms; more preferably a phenyl, 1-naphthyl or 2-naphthyl group; and most preferably a phenyl or 2-naphthyl group. Where Ar represents a substituted aryl group which is substituted with at least one substituent selected from the group consisting of substituents (a), this aryl group is preferably substituted with from one to five of said substituents, and more preferably with from one to three of said substituents. When more than one substituent is present on the aryl group, these substituent may be the same or different.

Where substituent (a) represents an alkyl group, this may be a straight or branched chain alkyl group having from 1 to 4 carbon atoms. Examples of such alkyl groups include: the methyl, ethyl, propyl, isopropyl, butyl, isobutyl, sec-butyl and t-butyl groups.

Where substituent (a) represents an alkoxy group, this may be a straight or branched chain alkoxy group having from 1 to 4 carbon atoms. Examples of such groups include: the methoxy, ethoxy, propoxy, isopropoxy, butoxy, isobutoxy, sec-butoxy and t-butoxy groups.

Where substituent (a) represents a haloalkyl group, the alkyl component may be straight or branched chain and has from 1 to 4 carbon atoms, particularly 1 or 2 carbon atoms, and preferably has from 1 to 3 halogen atoms which may be the same or different. Examples of such haloalkyl groups include the trifluoromethyl, trichloromethyl, difluoromethyl, dichloromethyl, dibromomethyl, 2,2,2-trichloroethyl, 2,2,2-trifluoroethyl, 2-fluoroethyl, 2,2-dibromoethyl, 3-chloropropyl, 3,3,3-trifluoropropyl and 4-fluorobutyl groups, of which we prefer alkyl groups having from 1 to 3 carbon atoms which are substituted by from 1 to 3 halogen atoms (and, where there are 2 or 3 halogen atoms, these are the same), more preferably the methyl or ethyl groups which are substituted by from 1 to 3 fluorine or chlorine atoms; the most preferred specific group is the trifluoromethyl group.

Where substituent (a) represents a halogen atom, this may be a fluorine, chlorine, iodine or bromine atom, preferably a chlorine or fluorine atom.

Examples of the group Ar when this is a $C_6$-$C_{10}$ aryl group substituted with from 1 to 5 substituents, which substituents may be the same or different, include: the 2-chlorophenyl, 3-chlorophenyl, 3-t-butylphenyl, 3-isopropylphenyl, 3-ethylphenyl, 4-chlorophenyl, 2,4-dichlorophenyl, 3,5-dichlorophenyl, 2,6-difluorophenyl, 2-chloro-4-fluorophenyl, 2-chloro-6-fluorophenyl, 3-chloro-4-fluorophenyl, 3-bromophenyl, 4-fluorophenyl, 3-fluorophenyl, 2-fluorophenyl, 3-methylphenyl, 4-isopropylphenyl, 3-methoxyphenyl, 2-methoxyphenyl, 4-methoxyphenyl, 3,5-dimethoxyphenyl, 2,5-dimethoxyphenyl, 3,4,6-trimethylphenyl, 3-fluoro-4-methoxyphenyl, 3-methyl-4-methoxyphenyl, 3-ethoxyphenyl, 4-ethoxyphenyl, 3,4-diethoxyphenyl, 2,5-dimethyl-4-methoxyphenyl, 3,5-dimethyl-4-hydroxyphenyl, 3,5-di-t-butyl-4-hydroxyphenyl, 5-bromo-2-ethoxyphenyl, 3,4,5-trimethoxyphenyl, 2,4,5-trimethoxyphenyl, 3-trifluoromethylphenyl, 4-trifluoromethylphenyl, 2,5-dimethoxy-3,4,6-trimethylphenyl and 2-methoxy-1-naphthyl group.

When Y is a group of formula —A—COOH, the compounds of the present invention necessarily contain a carboxy group. These compounds are acids and can thus form salts and esters. There is no particular restriction upon the nature of such salts and esters, provided that, where they are intended for therapeutic use, they should be "pharmaceutically acceptable", which, as is well known to those skilled in the art, means that they should not have a reduced activity (or unacceptably reduced activity) or an increased toxicity (or unacceptably increased toxicity) as compared with the free acids. Where the compounds are intended for non-therapeutic use, for example as intermediates in the preparation of other compounds, even these restrictions do not apply.

Examples of ester groups include:

- alkyl groups having from 1 to 20 carbon atoms, more preferably from 1 to 10 carbon atoms, still more preferably from 1 to 7 carbon atoms and most preferably from 1 to 5 carbon atoms, such as those exemplified above in relation to the alkyl groups which may be represented by R and higher alkyl groups as are well known in the art, such as the nonyl, decyl, undecyl, dodecyl, tridecyl, pentadecyl, octadecyl, nonadecyl and icosyl groups, preferably the methyl, ethyl, propyl, isopropyl, butyl, isobutyl, t-butyl and pentyl groups, but most preferably the methyl, ethyl and t-butyl groups;
- cycloalkyl groups having from 3 to 7 carbon atoms, for example the cyclopropyl, cyclobutyl, cyclopentyl, cyclohexyl and cycloheptyl groups;
- aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents (a) defined and exemplified above, although the unsubstituted groups are preferred; in general, we prefer those aralkyl groups having a total of from 7 to 9 carbon atoms; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;
- alkenyl groups having from 2 to 10 carbon atoms, more preferably from 3 to 10 carbon atoms and still more preferably from 3 to 5 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 1-octenyl, 1-nonenyl and 1-decenyl groups, of which the vinyl, allyl, 2-methylallyl, 1-propenyl, isopropenyl and butenyl groups are preferred, the allyl and 2-methylallyl groups being most preferred;
- halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the chloromethyl, bromomethyl, iodomethyl, fluoromethyl, trichloromethyl, trifluoromethyl, dichloromethyl, difluoromethyl, 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;
- substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents (a) defined and exemplified above, for example a 2-trimethylsilylethyl group;
- phenyl groups, in which the phenyl group is unsubstituted or substituted, preferably with at least one alkyl group having from 1 to 4 carbon atoms or acylamino group, for example the phenyl, tolyl and benzamidophenyl groups;
- phenacyl groups, which may be unsubstituted or have at least one of substituents (a) defined and exemplified above, for example the phenacyl group itself or the p-bromophenacyl group;
- cyclic and acyclic terpenyl groups, for example the geranyl, neryl, linalyl, phytyl, menthyl (especially m- and p-menthyl), thujyl, caryl, pinanyl, bornyl, norcaryl, norpinanyl, norbornyl, menthenyl, camphenyl and norbornenyl groups;
- alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;
- aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;
- cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the cyclohexylacetoxymethyl, 1-(cyclohexylacetoxy)ethyl, 1-(cyclohexylacetoxy)propyl, 2-methyl-1-(cyclohexylacetoxy)propyl, cyclopentylacetoxymethyl, 1-(cyclopentylacetoxy)ethyl, 1-(cyclopentylacetoxy)propyl and 2-methyl-1-(cyclopentylacetoxy)propyl groups;
- alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy) ethyl and 1-(1,1-dipropylbutoxycarbonyloxy)ethyl groups, and other alkoxycarbonyloxyalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl, in which the phenyl group may be substituted by at least one of substituents (a), defined and exemplified above, (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer: the alkyl esters, especially those in which the alkyl group has from 1 to 4 carbon atoms, such as the methyl, ethyl, propyl, isopropyl, s-butyl, t-butyl, butyl and isobutyl esters.

The compounds of the present invention in which Y is a hydrogen atom or a group of formula —A—COOH can also form salts. Examples of such salts include: salts with an alkali metal, such as sodium, potassium or lithium; salts with an alkaline earth metal, such as magnesium, barium or calcium; salts with another metal, such as aluminum; ammonium salts; organic base salts, such as a salt with methylamine, dimethylamine, triethylamine, diisopropylamine, guanidine, aminoguanidine or dicyclohexylamine; and salts with a basic amino acid, such as lysine or arginine.

The compounds of the present invention can exist in the form of various stereoisomers, as shown in formula (A):

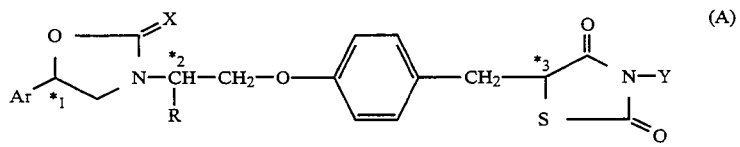

in which R, Ar, X and Y are as defined above. There are three asymmetric carbon atoms marked *1, *2 and *3 in formula (A). Although these are all represented herein by a single molecular formula, the present invention includes both the individual, isolated isomers and mixtures (where the amounts of the isomers may be equal or different), including racemates thereof. Where stereospecific synthesis techniques are employed or optically active compounds are employed as starting materials, individual isomers my be prepared directly; on the other hand, if a mixture of isomers is prepared, the individual isomers may be obtained by conventional resolution techniques.

Of the compounds of the invention, we prefer those isomers in which the asymmetric carbon atoms marked by *1 and *2 are in the R-configuration.

The compounds of the present invention in which Y represents a hydrogen atom may also exist as tautomeric isomers. The relationship between these tautomers is shown as follows, in which R, X and Ar are as defined above.

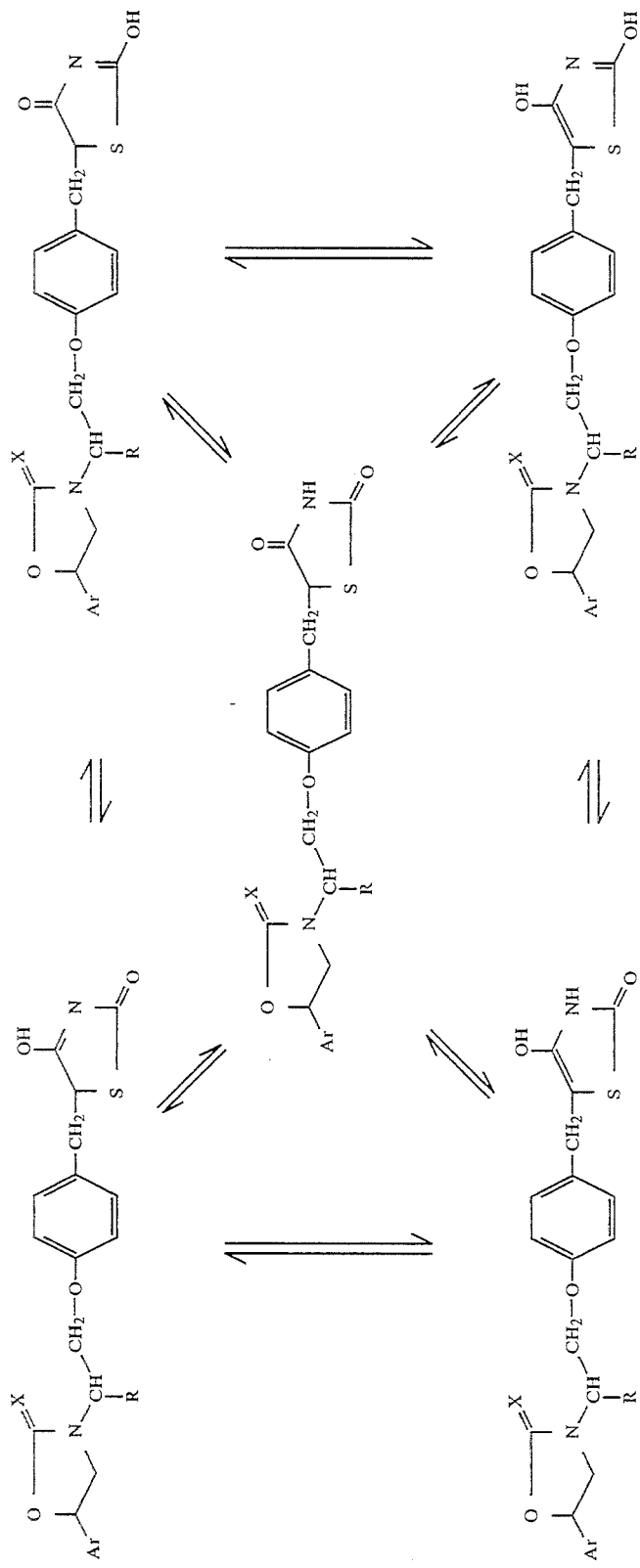

Although these are all represented herein by a single molecular formula, the present invention includes both the individual, isolated isomers and mixtures thereof (where the amounts of isomers may be equal or different).

(1) The preferred compounds of the present invention are those compounds of formula (I) and salts thereof, in which:

R represents an alkyl group having from 1 to 6 carbon atoms;

X represents an oxygen atom or a sulfur atom;

Y represents a hydrogen atom or a group of formula —A—COOH, in which A represents an alkylene group having from 1 to 4 carbon atoms;

Ar represents an aryl group having from 6 to 10 ring carbon atoms, or an aryl group having from 6 to 10 ring carbon atoms substituted with from 1 to 5 substituents, which may be the same or different, selected from the group consisting of substituents (a), defined and exemplified above; and when Y represents the group of formula —A—COOH, the $C_1$ to $C_4$ alkyl esters thereof.

(2) More preferred compounds of the present invention are those compounds of formula (I) and salts thereof, in which:

R represents an alkyl group having 1 to 4 carbon atoms;

X represents an oxygen atom or a sulfur atom;

Y represents a hydrogen atom or a group of formula —A—COOH, in which A represents a methylene or an ethylene group; and Ar represents an unsubstituted phenyl group, an unsubstituted naphthyl group or a phenyl or napthyl group substituted with from 1 to 5 substituents, which may be the same or different, selected from the group consisting of substituents (a), as defined and exemplified above; and when Y represents a group of formula —A—COOH, the $C_1$ to $C_4$ alkyl esters thereof.

(3) Still more preferred compounds of the present invention are those compounds of formula (I) in which:

R represents an alkyl group having 1 to 4 carbon atoms;

X represents an oxygen or sulfur atom;

Y represents a hydrogen atom or a group of formula: —CH$_2$—COOH;

Ar represents an unsubstituted phenyl group, an unsubstituted naphthyl group or a phenyl group substituted by from 1 to 5 substituents, which are the same or different, selected from the group consisting of substituents (a'), as defined below;

substituents (a'): halogen atoms, trifluoromethyl groups, hydroxy groups, alkyl groups having from 1 to 4 carbon atoms and alkoxy groups having 1 or 2 carbon atoms; and when Y represents the group of formula —CH$_2$—COOH, the $C_1$ to $C_4$ alkyl esters thereof.

(4) The most preferred compounds of the present invention are those compounds of formula (I) in which:

R represents a methyl or an ethyl group:

X represents an oxygen or sulfur atom:

Y represents a hydrogen atom or a group of formula: —CH$_2$—COOH;

Ar represents a phenyl, 2-chlorophenyl, 3-chlorophenyl, 4-chlorophenyl 3-bromophenyl, 3-fluorophenyl, 3-trifluoromethylphenyl, 3-methylphenyl, 3-methoxyphenyl, 3,5-dichlorophenyl, 3,5-di-t-butyl-4-hydroxyphenyl, 3,4,5-trimethoxyphenyl, 3-chloro-4-fluorophenyl, 2,5-dimethoxy-3,4,6-trimethylphenyl, 3,5-dimethyl-4-hydroxyphenyl or 2-naphthyl group; and when Y represents the group of formula —CH$_2$—COOH, the methyl and ethyl esters thereof.

Specific examples of the compounds of the present invention are those compounds of formula (I-1) and (I-2), in which the substituents are as defined in the respective one of Tables 1 and 2, below, i.e. Table 1 relates to formula (I-1) and Table 2 relates to formula (I-2). In the Tables, the following abbreviations are used:

| | |
|---|---|
| Bu | butyl |
| iBu | isobutyl |
| tBu | t-butyl |
| sBu | sec-butyl |
| Et | ethyl |
| Me | methyl |
| MeO | methoxy |
| Np | naphthyl |
| Ph | phenyl |
| Pr | propyl |
| iPr | isopropyl |
| Pn | pentyl |
| Tfm | trifluoromethyl. |

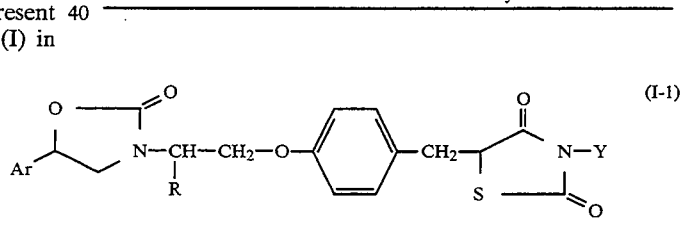

(I-1)

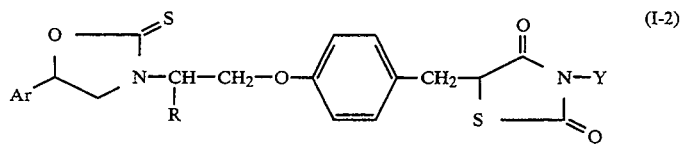

(I-2)

TABLE 1

| Compound No. | Ar | R | Y |
|---|---|---|---|
| 1 | Ph— | Me | H |
| 2 | Ph— | Me | CH$_2$COOH |
| 3 | Ph— | Me | CH$_2$COOMe |
| 4 | Ph— | Me | CH$_2$COOtBu |
| 5 | 3-Cl—Ph— | Me | H |
| 6 | 3-Cl—Ph— | Me | CH$_2$COOH |
| 7 | 3-Cl—Ph— | Me | CH$_2$COOMe |
| 8 | 3-Cl—Ph— | Me | CH$_2$COOtBu |
| 9 | 3-Cl—Ph— | Et | H |
| 10 | 3-Cl—Ph— | iPr | H |
| 11 | 3-F—Ph— | Me | H |

TABLE 1-continued

| Compound No. | Ar | R | Y |
|---|---|---|---|
| 12 | 3-Tfm—Ph— | Me | H |
| 13 | 3-Tfm—Ph— | Me | CH$_2$COOMe |
| 14 | 3-Tfm—Ph— | Me | CH$_2$COOtBu |
| 15 | 3-Me—Ph— | Me | H |
| 16 | 3-MeO—Ph— | Me | H |
| 17 | 3,5-ditBu-4-HO—Ph— | Me | H |
| 18 | 3,5-diMe-4-HO—Ph— | Pn | CH$_2$COOEt |
| 19 | 2,5-diMeO-3,4,6-triMe—Ph— | Me | H |
| 20 | 3,5-ditBu-4-HO—Ph— | Me | CH$_2$COOMe |
| 21 | 3-Br—Ph— | Me | CH$_2$COOtBu |
| 22 | 3-Tfm—Ph— | Me | CH$_2$COOH |
| 23 | 3-Tfm—Ph— | Et | H |
| 24 | 3-Tfm—Ph— | Et | CH$_2$COOtBu |
| 25 | 3-Tfm—Ph— | iPr | H |
| 26 | 3-Cl—Ph— | iPr | CH$_2$COOPr |
| 27 | 3,5-diMe-4-HO—Ph— | Me | H |
| 28 | 3,5-diMe-4-HO—Ph— | Me | CH$_2$COOMe |
| 29 | 3,5-diMe-4-HO—Ph— | Pr | H |
| 30 | 3,5-ditBu-4-HO—Ph— | Bu | H |
| 31 | 3,5-ditBu-4-HO—Ph— | Me | CH$_2$COOMe |
| 32 | 3,5-ditBu-4-HO—Ph— | iBu | CH$_2$COOH |
| 33 | 3-F—Ph— | Et | H |
| 34 | 3-F—Ph— | Me | CH$_2$COOH |
| 35 | 3-F—Ph— | Me | CH$_2$COOMe |
| 36 | 3-F—Ph— | Me | CH$_2$COOiPr |
| 37 | 3-F—Ph— | sBu | H |
| 38 | 3-F—Ph— | tBu | CH$_2$COOsBu |
| 39 | 3-F—Ph— | Pn | CH$_2$COOBu |
| 40 | 3-F—Ph— | Me | CH$_2$COOiBu |
| 41 | 3-Et—Ph— | Me | H |
| 42 | 3-iPr—Ph— | Me | H |
| 43 | 3-tBu—Ph— | Me | H |
| 44 | 3-tBu—Ph— | Me | CH$_2$COOMe |
| 45 | 1-Np— | Me | H |
| 46 | 1-Np— | Me | CH$_2$COOMe |
| 47 | 1-Np— | Bu | CH$_2$COOsBu |
| 48 | 2-Np— | Me | H |
| 49 | 2-Np— | Me | CH$_2$COOMe |
| 50 | 2-Np— | sBu | CH$_2$COOH |
| 51 | 3-Cl—Ph— | iBu | H |
| 52 | 3-Cl—Ph— | Me | CH$_2$CH$_2$COOEt |
| 53 | 3-Cl—Ph— | Pr | H |
| 54 | 3-Cl—Ph— | Me | CH$_2$CH$_2$CH$_2$COOMe |
| 55 | 3-Cl—Ph— | Et | CH$_2$CH$_2$CH$_2$CH$_2$COOEt |
| 56 | 3,5-diMe-4-HO—Ph— | Me | CH$_2$CH$_2$COOPr |
| 57 | 3,5-diMe-4-HO—Ph— | Et | H |
| 58 | 3-Cl-4-F—Ph— | Me | H |
| 59 | 3-Cl-4-F—Ph— | Et | H |
| 60 | 3-Cl-4-F—Ph— | Pr | H |
| 61 | 3-Cl-4-F—Ph— | Me | CH$_2$COOMe |
| 62 | 3-Cl-4-F—Ph— | iBu | H |
| 63 | 3,5-diCl—Ph— | Me | H |
| 64 | 3,5-diCl—Ph— | iPr | CH$_2$CH$_2$COOBu |
| 65 | 3-Me—Ph— | Me | CH$_2$COOMe |
| 66 | 2-Cl—Ph— | Me | H |
| 67 | 4-Cl—Ph— | Me | H |
| 68 | 3-MeO—Ph— | Me | CH$_2$COOiPr |
| 69 | 3,4,5-triMeO—Ph— | Me | H |
| 70 | 4-EtO—Ph— | Me | H |
| 71 | 3-Cl—Ph— | Me | CH(Me)—COOEt |
| 72 | 3,5-diMe-4-HO—Ph— | Me | CH(Me)—COOMe |
| 73 | 2,5-diMeO—Ph— | Me | H |
| 74 | 3,5-diMeO—Ph— | Et | CH$_2$COOEt |
| 75 | 4-MeO—Ph— | Me | H |
| 76 | 2-MeO—Ph— | Me | H |
| 77 | 2-F—Ph— | Me | H |
| 78 | 4-F—Ph— | Pr | CH$_2$CH$_2$COOiPr |
| 79 | 2,4,5-triMeO—Ph— | Me | H |
| 80 | 2,4-diCl—Ph— | Me | H |
| 81 | 2,4-diCl—Ph— | Et | H |
| 82 | 2-Cl-6-F—Ph— | Me | H |
| 83 | 2-Cl-6-F—Ph— | Me | CH$_2$COOMe |
| 84 | 3-F-4-MeO—Ph— | Me | H |
| 85 | 3-F-4-MeO—Ph— | iBu | H |
| 86 | 3-F-4-MeO—Ph— | Et | CH$_2$CH$_2$CH$_2$CH$_2$CH$_2$COOMe |
| 87 | 3-Me-4-MeO—Ph— | Me | H |
| 88 | 3-EtO—Ph— | Me | H |
| 89 | 2,5-diMe-4-MeO—Ph— | Me | H |
| 90 | 2,5-diMe-4-MeO—Ph— | Et | CH$_2$COOtBu |
| 91 | 4-Tfm—Ph— | Me | H |
| 92 | 2,6-diF—Ph— | Me | H |
| 93 | 2,6-diF—Ph— | Me | CH$_2$COOEt |
| 94 | 4-iPr—Ph— | Me | H |
| 95 | 4-iPr—Ph— | Pn | H |
| 96 | 5-Br-2-EtO—Ph— | Me | H |
| 97 | 3,4-diEtO—Ph— | Me | H |
| 98 | 2-MeO-1-Np— | Me | CH$_2$COOEt |
| 99 | 3,4,6-triMe—Ph— | Me | H |
| 100 | 2-Np— | iBu | H |

TABLE 2

| Compd No. | Ar | R | Y |
|---|---|---|---|
| 101 | Ph— | Me | H |
| 102 | Ph— | Me | CH$_2$COOH |
| 103 | Ph— | Me | CH$_2$COOMe |
| 104 | Ph— | Me | CH$_2$COOtBu |
| 105 | 3-Cl—Ph— | Me | H |
| 106 | 3-Cl—Ph— | Me | CH$_2$COOH |
| 107 | 3-Cl—Ph— | Me | CH$_2$COOMe |
| 108 | 3-Cl—Ph— | Me | CH$_2$COOtBu |
| 109 | 3-Cl—Ph— | Et | H |
| 110 | 3-Cl—Ph— | iPr | H |
| 111 | 3-F—Ph— | Me | H |
| 112 | 3-Tfm—Ph— | Me | H |
| 113 | 3-Tfm—Ph— | Me | CH$_2$COOMe |
| 114 | 3-Tfm—Ph— | Me | CH$_2$COOtBu |
| 115 | 3-Me—Ph— | Me | H |
| 116 | 3-MeO—Ph— | Me | H |
| 117 | 3,5-ditBu-4-HO—Ph— | Me | H |
| 118 | 3,5-diMe-4-HO—Ph— | Pn | CH$_2$COOEt |
| 119 | 2,5-diMeO-3,4,6-triMe—Ph— | Me | H |
| 120 | 3,5-ditBu-4-HO—Ph— | Me | CH$_2$COOMe |
| 121 | 3-Br—Ph— | Me | CH$_2$COOtBu |
| 122 | 3-Tfm—Ph— | Me | CH$_2$COOH |
| 123 | 3-Tfm—Ph— | Et | H |
| 124 | 3-Tfm—Ph— | Et | CH$_2$COOtBu |
| 125 | 3-Tfm—Ph— | iPr | H |
| 126 | 3-Cl—Ph— | iPr | CH$_2$COOPr |
| 127 | 3,5-diMe-4-HO—Ph— | Me | H |
| 128 | 3,5-diMe-4-HO—Ph— | Me | CH$_2$COOMe |
| 129 | 3,5-diMe-4-HO—Ph— | Pr | H |
| 130 | 3,5-ditBu-4-HO—Ph— | Bu | H |
| 131 | 3,5-ditBu-4-HO—Ph— | Me | CH$_2$COOMe |
| 132 | 3,5-ditBu-4-HO—Ph— | iBu | CH$_2$COOH |
| 133 | 3-F—Ph— | Et | H |
| 134 | 3-F—Ph— | Me | CH$_2$COOH |

TABLE 2-continued

| Compd No. | Ar | R | Y |
|---|---|---|---|
| 135 | 3-F—Ph— | Me | CH$_2$COOMe |
| 136 | 3-F—Ph— | Me | CH$_2$COOiPr |
| 137 | 3-F—Ph— | sBu | H |
| 138 | 3-F—Ph— | tBu | CH$_2$COOsBu |
| 139 | 3-F—Ph— | Pn | CH$_2$COOBu |
| 140 | 3-F—Ph— | Me | CH$_2$COOiBu |
| 141 | 3-Et—Ph— | Me | H |
| 142 | 3-iPr—Ph— | Me | H |
| 143 | 3-tBu—Ph— | Me | H |
| 144 | 3-tBu—Ph— | Me | CH$_2$COOMe |
| 145 | 1-Np— | Me | H |
| 146 | 1-Np— | Me | CH$_2$COOMe |
| 147 | 1-Np— | Bu | CH$_2$COOsBu |
| 148 | 2-Np— | Me | H |
| 149 | 2-Np— | Me | CH$_2$COOMe |
| 150 | 2-Np— | sBu | CH$_2$COOH |
| 151 | 3-Cl—Ph— | iBu | H |
| 152 | 3-Cl—Ph— | Me | CH$_2$CH$_2$COOEt |
| 153 | 3-Cl—Ph— | Pr | H |
| 154 | 3-Cl—Ph— | Me | CH$_2$CH$_2$CH$_2$COOMe |
| 155 | 3-Cl—Ph— | Et | CH$_2$CH$_2$CH$_2$CH$_2$COOEt |
| 156 | 3,5-diMe-4-HO—Ph— | Me | CH$_2$CH$_2$COOPr |
| 157 | 3,5-diMe-4-HO—Ph— | Et | H |
| 158 | 3-Cl-4-F—Ph— | Me | H |
| 159 | 3-Cl-4-F—Ph— | Et | H |
| 160 | 3-Cl-4-F—Ph— | Pr | H |
| 161 | 3-Cl-4-F—Ph— | Me | CH$_2$COOMe |
| 162 | 3-Cl-4-F—Ph— | iBu | H |
| 163 | 3,5-diCl—Ph— | Me | H |
| 164 | 3,5-diCl—Ph— | iPr | CH$_2$CH$_2$COOBu |
| 165 | 3-Me—Ph— | Me | CH$_2$COOMe |
| 166 | 2-Cl—Ph— | Me | H |
| 167 | 4-Cl—Ph— | Me | H |
| 168 | 3-MeO—Ph— | Me | CH$_2$COOiPr |
| 169 | 3,4,5-triMeO—Ph— | Me | H |
| 170 | 4-EtO—Ph— | Me | H |
| 171 | 3-Cl—Ph— | Me | CH(Me)—COOEt |
| 172 | 3,5-diMe-4-HO—Ph— | Me | CH(Me)—COOMe |
| 173 | 2,5-diMeO—Ph— | Me | H |
| 174 | 3,5-diMeO—Ph— | Et | CH$_2$COOEt |
| 175 | 4-MeO—Ph— | Me | H |
| 176 | 2-MeO—Ph— | Me | H |
| 177 | 2-F—Ph— | Me | H |
| 178 | 4-F—Ph— | Pr | CH$_2$CH$_2$COOiPr |
| 179 | 2,4,5-triMeO—Ph— | Me | H |
| 180 | 2,4-diCl—Ph— | Me | H |
| 181 | 2,4-diCl—Ph— | Et | H |
| 182 | 2-Cl-6-F—Ph— | Me | H |
| 183 | 2-Cl-6-F—Ph— | Me | CH$_2$COOMe |
| 184 | 3-F-4-MeO—Ph— | Me | H |
| 185 | 3-F-4-MeO—Ph— | iBu | H |
| 186 | 3-F-4-MeO—Ph— | Et | CH$_2$CH$_2$CH$_2$CH$_2$CH$_2$COOMe |
| 187 | 3-Me-4-MeO—Ph— | Me | H |
| 188 | 3-EtO—Ph— | Me | H |
| 189 | 2,5-diMe-4-MeO—Ph— | Me | H |
| 190 | 2,5-diMe-4-MeO—Ph— | Et | CH$_2$COOtBu |
| 191 | 4-Tfm—Ph— | Me | H |
| 192 | 2,6-diF—Ph— | Me | H |
| 193 | 2,6-diF—Ph— | Me | CH$_2$COOEt |
| 194 | 4-iPr—Ph— | Me | H |
| 195 | 4-iPr—Ph— | Pn | H |
| 196 | 5-Br-2-EtO—Ph— | Me | H |
| 197 | 3,4-diEtO—Ph— | Me | H |
| 198 | 2-MeO-1-Np— | Me | CH$_2$COOEt |
| 199 | 3,4,6-triMe—Ph— | Me | H |
| 200 | 2-Np— | iBu | H |

Of the compounds exemplified above, preferred are Compounds No. 5, 6, 7, 11, 12, 13, 19, 20, 27, 35, 48, 105, 106, 107, 111, 112, 113, 119, 120, 127, 135 and 148 and the pharmaceutically acceptable salts thereof.

More preferred compounds are Compounds No. 5, 7, 12, 13, 19, 27, 48, 105, 107, 112, 113, 119, 127 and 148 and the pharmaceutically acceptable salts thereof.

Most preferred are the following compounds:

5. 3-{2-[4-(2,4-Dioxothiazolidin-5-ylmethyl)phenoxy]-1-methylethyl}-5-(3-chlorophenyl)oxazolidin-2-one;

7. 3-{2-[4-(3-Methoxycarbonylmethyl-2,4-dioxothiazolidin-5-ylmethyl)phenoxy]-1-methylethyl}-5-(3-chlorophenyl)oxazolidin-2-one;

105. 3-{2-[4-(2,4-Dioxothiazolidin-5-ylmethyl)phenoxy]-1-methylethyl}-5-(3-chlorophenyl)oxazolidine-2-thione; and 107. 3-{2-[4-(3-Methoxycarbonylmethyl-2,4-dioxothiazolidin-5-ylmethyl)phenoxy]-1-methylethyl}-5-(3-chlorophenyl)oxazolidine-2-thione;

and the pharmaceutically acceptable salts thereof.

The compounds of the present invention may be prepared by a variety of methods well known for preparation of compounds of this type. For example, in general terms, they may be prepared by:

(a) reacting a compound of formula (V):

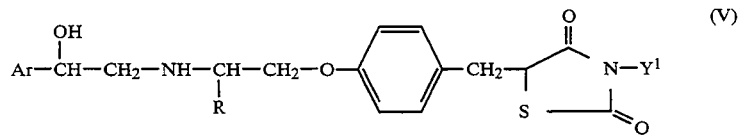

(in which Ar and R are as defined above and $Y^1$ represents any of the groups represented by Y, as defined above, or an amino-protecting group) with a carbonylating or thiocarbonylating agent; and (b) if desired, deprotecting the resulting compound; and (c) if desired, hydrolyzing, salifying or esterifying the compound obtained to produce a compound of formula (I) or a salt or ester thereof.

More particularly, the compounds of the present invention can be prepared by any one of Methods 1 to 5, as described hereinafter.

METHOD 1

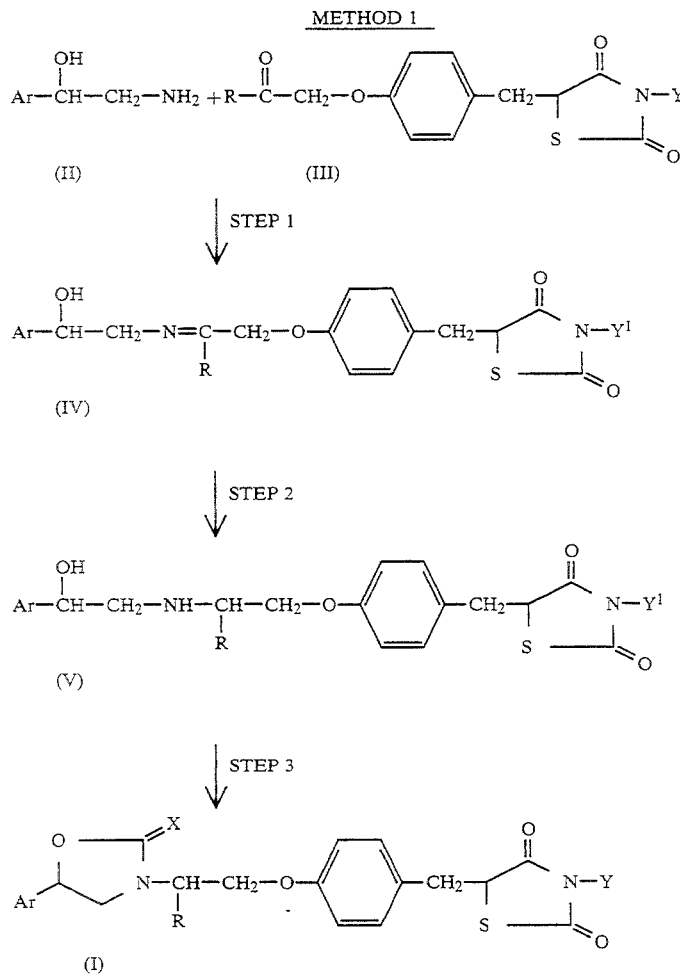

In the above formulae, Ar, R, X, $Y^1$ and $Z^1$ are as defined above. When $Y^1$ is a protecting group, this may be, for example, a triphenylmethyl (trityl) group.

Step 1

In this step, an amino-alcohol of formula (II) [Collins, J. Med. Chem., 13 (1970) 674] is reacted with a compound of formula (III). The compound of formula (III) can itself be prepared using conventional procedures, for example by the reaction of a halogenated acetone derivative with a phenol compound.

The reaction of the amino-alcohol of formula (II) with the compound of formula (III) may, if desired, be carried out in the presence of a dehydrating agent, such as anhydrous sodium carbonate, anhydrous potassium carbonate, anhydrous sodium sulfate, anhydrous calcium chloride or anhydrous magnesium sulfate, or in the presence of a molecular sieve, or may be carried out in the absence of any such material. The reaction is normally and preferably carried out in the presence of a solvent. There is no particular restriction on the nature of the solvent to be employed, provided that it has no adverse effect upon the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers such as diethyl ether, tetrahydrofuran or dioxane; amides such as dimethylformamide, dimethylacetamide or hexamethylphosphoric triamide; alcohols such as methanol or ethanol; sulfoxides such as dimethyl sulfoxide; sulfolane; or a mixture of any two or more of these solvents. We generally prefer to carry out the reaction in the presence of a hydrocarbon or alcohol solvent, and most preferably in the presence of benzene. The reaction can take place over a wide range of temperatures, and the precise reaction temperature is not critical to the invention. In general, we find it convenient to carry out the reaction at a temperature between ice-cooling and the reflux temperature of the solvent (if any) used, and more preferably, whilst heating under reflux. The time required for the reaction may also vary widely, depending on many factors, notably the reaction temperature and the nature of the reagents. However, provided that the reaction is effected under the preferred conditions outlined above, a period of from 0.5 to 10 hours, more preferably from 1 to 5 hours, and most preferably from 1 to 3 hours, will usually suffice.

Step 2

The resulting compound of formula (IV) may then be reduced to produce a compound of formula (V).

The reduction reaction may be carried out by contacting the compound of formula (IV) with a suitable reducing agent or by hydrogenation of the compound of formula (IV) in the presence of a catalyst.

When the reaction is carried out in the presence of a reducing reagent, there is no particular restriction on the nature of the reducing agent employed in this reaction. Examples of especially suitable reducing agents include the metal borohydrides, especially alkali metal borohydrides, such as lithium borohydride, sodium borohydride; or sodium cyanoborohydride and lithium aluminum hydride or diisobutylaluminum hydride, of which we particularly prefer sodium borohydride and sodium cyanoborohydride. The amount of reducing agent is not critical to the reaction, although, for economy, it is preferred that the amount should be at least equimolar with respect to the compound of formula (IV). In general the reaction is normally carried out using from 1 to 50 moles, and preferably a large excess of the reducing agent, per mole of the compound of formula (IV). The reaction is normally and preferably carried out in the presence of a solvent. There is no particular restriction on the nature of the solvent to be employed, provided that it has no adverse effect on the reaction or on the reagents involved, and that it can dissolve the reagents, at least to some extent. Examples of the solvents used include: hydrocarbons, such as benzene, toluene, xylene, hexane or heptane; ethers, such as diethyl ether, tetrahydrofuran or dioxane; amides, such as dimethylformamide, dimethylacetamide or hexamethylphosphoric triamide; alcohols, such as methanol, ethanol or isopropanol; or a mixture of any two or more of these solvents. Of these solvents, we prefer to use an alcohol. The reaction can take place over a wide range of temperatures, and the precise reaction temperature is not critical to the invention. In general, we find it convenient to carry out the reaction at a temperature between ice-cooling and some heating, preferably between ice-cooling and 50° C. The time required for the reaction may also vary widely, depending on many factors, notably the reaction temperature and the nature of the reagents and of the solvent. However, provided that the reaction is effected under the preferred conditions outlined above, a period of from 30 minute to several days, preferably of from 1 hour to 1 day, will usually suffice.

Where reduction is carried out by hydrogenation in the presence of catalyst, the catalyst used may be any catalyst commonly used for catalytic reduction, and the nature of the catalyst is not critical to the present invention. Examples of preferred catalysts include palladium-on-charcoal or platinum oxide. In general, the reaction is preferably carried out in the presence of a solvent, the nature of which is not critical, provided that it has no adverse effect upon the reaction and that it can dissolve the reagents, at least to some extent. Examples of suitable solvents include: ethers, such as diethyl ether, tetrahydrofuran or dioxane; amides, such as dimethylformamide or dimethylacetamide; alcohols, such as methanol, ethanol or isopropanol; organic acid esters, such as methyl acetate or ethyl acetate; and mixtures of any two or more of the solvents described above. Where a palladium catalyst is used, the catalytic hydrogenation is preferably carried out under from medium to high pressure, preferably at from 1 to 5 kg/cm². Where a platinum catalyst is used, the hydrogenation is preferably carried out at atmospheric pressure. The reaction will take place over a wide range of temperatures, and the precise reaction temperature chosen is not critical to the invention. In general, we find it convenient to carry out the reaction at a temperature in the range of from room temperature to 50° C. It is also preferably carried out in the presence of an alcoholic solvent, particularly methanol or ethanol.

Step 3

A compound of formula (I) can be prepared by reaction of a compound of formula (V) with a carbonylating agent or thiocarbonylating agent. The reaction of a compound of formula (V) with a carbonylating agent results in a product in which X is an oxygen atom, and the reaction of a compound of formula (V) with a thiocarbonylating agent results in a product in which X is a sulphur atom. There is no particular restrction on the nature of the carbonylating or thiocarbonylating agent employed in this reaction and examples of such agents include: phosgene; diphosgene; triphosgene; carbonyldiimidazole; chloroformic esters, such as ethyl chloroformate; thiophosgene and thiocarbonyldiimidazole. The reaction may, if desired, be carried out in the presence of a base, in order to remove any acid formed during the reaction. Where such a base is used, the nature of the base is not critical to the present invention. Generally, we prefer to use a base such as: an organic base, such as triethylamine, diisopropylethylamine or pyridine; or an inorganic base, such as sodium carbonate or potassium carbonate. The reaction is normally and preferably carried out in the presence of a solvent, the precise nature of which is not essential to the present invention, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride, 1,2-dichloroethane or carbon tetrachloride; ethers, such as diethyl ether, tetrahydrofuran or dioxane; amides, such as dimethylformamide, dimethylacetamide or hexamethylphosphoric triamide; urea derivatives, such as N,N'-dimethylimidazolidinone; sulfoxides, such as dimethyl sulfoxide; nitriles, such as acetonitrile or propionitrile; sulfolane; or a mixture of any two or more of these solvents. The reaction can take place over a wide range of temperatures, and the exact reaction temperature is not critical to the invention. In general, we find it convenient to carry out the reaction at a temperature between ice-cooling and the reflux temperature of the solvent used, preferably a temperature of from ice-cooling to 50° C. The time required for the reaction may also vary widely, depending on, for example, the reaction temperature and the nature of the reagents and of the solvent used. However, provided that the reaction is performed under the preferred conditions outlined above, a period of from 30 minutes to 50 hours, preferably of from 5 to 50 hours, will usually suffice.

Where the compound of formula (II) is an optically active compound owing to the presence of asymmetric carbon atoms at the positions marked by *1 in the , compound of formula (A), the stereochemical integrity can be retained in the compound of formula (I). Moreover, in Step 2, where a conventional asymmetric hydrogenation reaction can be carried out, compounds of formula (I) can be prepared as a stereoisomer having an asymmetric carbon atom at the position marked by *2 in the general formula (A).

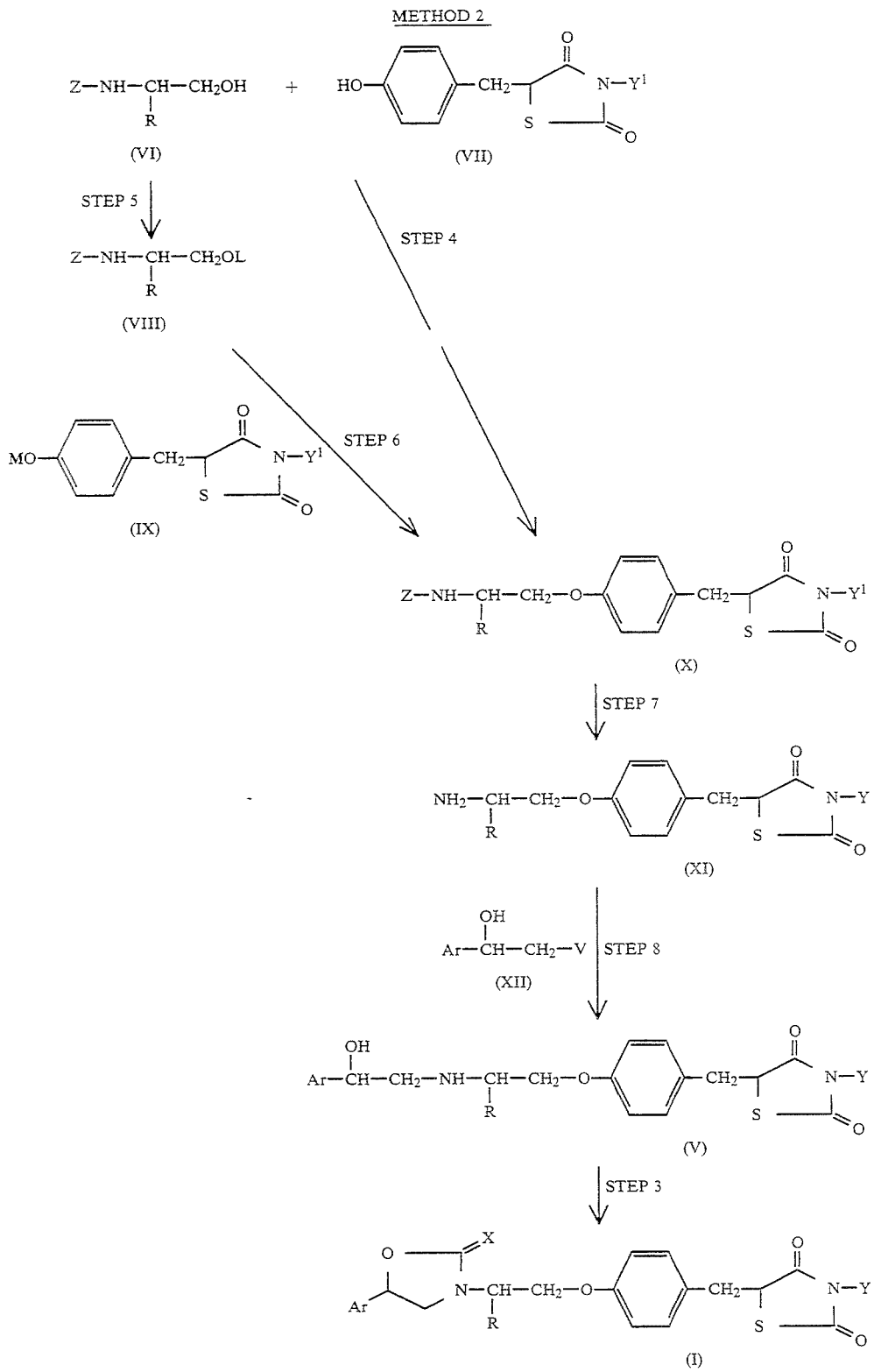

In the above formulae, Ar, R, X and $Y^1$ are as defined above; L represents an alkanesulfonyl group, such as a methanesulfonyl, ethanesulfonyl, propanesulfonyl or butanesulfonyl group; or an arylsulfonyl group, such as a toluenesulfonyl or napthalenesulfonyl group, preferably a p-toluenesulfonyl group; V represents a halogen atom, e.g. a chlorine, bromine or iodine atom; Z represents an amino-protecting group, for example an alkoxycarbonyl group or an aryloxycarbonyl group, such as a t-butoxycarbonyl group or a benzyloxycarbonyl group; and M represents an alkali metal, such as sodium or potassium.

Step 4

In this step, a compound of formula (X) is prepared by reacting an H-protected amino-alcohol of formula (VI) with a phenyl compound of formula (VII). This reaction may be carried out by conventional procedures, for example using the Mitsunobu reaction [O. Mitsunobu, Synthesis, 1 (1981)]. In general, the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; halogenated hydrocarbons, especially halogenated aliphatic hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; and mixtures of any two or more of the solvents described above. The reaction can take place over a wide range of temperatures, and the precise reaction temperature is not critical to the invention. In general, we find it convenient to carry out the reaction at a temperature of from that of an ice-water bath to some heating, more preferably from ice-cooling to 60° C. The time required for the reaction may also vary widely, depending on many factors, notably the reaction temperature and the nature of the reagents and solvent employed. However, provided that the reaction is effected under the preferred conditions outlined above, a period of from several hours to several days, more preferably from 5 hours to 3 days, will usually suffice.

Step 5

The compounds of formula (VIII) may be prepared by alkanesulfonylation or arylsulfonylation, preferably mesylation or tosylation, of a compound of formula (VI).

The reaction may, if desired, be carried out in the presence of a base, in order to remove any acid formed during the reaction, the nature of which is not critical to the present invention. Alternatively, the reaction may be carried out in the absence of a base. Examples of suitable bases include: alkali metal carbonates, such as sodium carbonate, sodium hydrogencarbonate, potassium carbonate; triethylamine and pyridine. The reaction is normally and preferably carried out in the presence of a solvent. There is no particular limitation on the nature of the solvent to be employed, provided that it has no adverse effect upon the reaction or on the reagents involved, and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; sulfoxides, such as dimethylsulfoxide; or a mixture of any two or more of the above solvents. The reaction can take place over a wide range of temperatures, and the precise reaction temperature is not critical to the present invention. In general, we find it convenient to carry out the reaction at a temperature between ice-cooling and some heating, preferably at a temperature between ice-cooling and 60° C. The time required for the reaction may also vary widely, depending on many factors, notably the reaction temperature and the nature of the reagents and of the solvent. However, provided that the reaction is effected under the preferred conditions outlined above, a period of from 1 hour to several days, for example from 1 hour to 1 day, will usually suffice.

The reaction is preferably carried out in the presence of triethylamine at a temperature of from ice-cooling to 60° C. and for a period of from 1 hour to 1 day.

Step 6

A compound of formula (X) can be prepared by reacting a compound of formula (VIII) with a compound of formula (IX).

The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, tetrahydrofuran or dioxane; amides, such as dimethylformamide, dimethylacetamide or hexamethylphosphoric triamide; or a mixture of any two or more of these solvents. The reaction may be carried out over a wide range of temperatures, and the precise reaction temperature is not critical to the present invention. In general, we find it convenient to carry out the reaction at a temperature between ice-cooling and some heating, preferably at a temperature of between ice-cooling and 60° C. The time required for the reaction may also vary widely, depending on many factors, notably the reaction temperature and the nature of the reagents and of the solvents. However, provided that the reaction is effected under the preferred conditions outlined above, a period of from 1 hour to several days, particularly from 1 hour to 1 day, will usually suffice.

The reaction is preferably carried out in the presence of a solvent at a temperature of from ice-cooling to 60° C., for a period of from 1 hour to 1 day.

Step 7

A compound of formula (XI) can be prepared by deprotection of a compound of the formula (X) to remove the protecting group Z and, if desired, to remove a protecting group $Y^1$. Deprotection can be performed using any conventional technique, such as according to the procedure described by T. W. Green in "Protective Groups in Organic Synthesis", John Wiley & Sons; and by J. F. W. McOmie in "Protective Groups in Organic Chemistry", Plenum Press, the disclosure of which is incorporated herein by reference.

Step 8

A compound of formula (V) is prepared by reacting a halohydrin compound of formula (XII) with an amino compound of formula (XI).

The reaction may, if desired, be carried out in the presence of a base, the nature of which is not critical to the present invention. Alternatively, the reaction may be carried out in the absence of a base. Examples of suitable bases, present in the reaction mixture to remove any acid formed during the reaction, include: alkali metal carbonates, such as sodium carbonate, sodium hydrogencarbonate and potassium carbonate; and triethylamine. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; alcohols, such as methanol, ethanol or isopropanol; sulfoxides, such as dimethyl sulfoxide; or a mixture of any two or more of the above solvents. The reaction may be carried out over a wide range of temperatures, and the precise reaction temperature is not critical to the present invention. In general, we find it convenient to carry out the reaction at room temperature, or with some heating, preferably at a temperature of from room temperature to 60° C. The time required for the reaction may also vary, depending on many factors, notably the reaction temperature and the nature of the reagents and of the solvent. However, provided that the reaction is effected under the preferred conditions outlined above, a period of from 1 hour to several days, particularly from 3 hours to 3 days, will usually suffice.

The reaction is preferably carried out in a solvent selected from the group consisting of alcohols, amides and sulfoxides at a temperature of from room temperature to 60° C., for a period of 3 hours to 3 days.

Step 3

A compound of formula (I) may then be prepared by reacting a compound of formula (V) with a carbonylating or thiocarbonylating agent, as described above.

Where the compound of formula (VI) is an optically active compound, owing to the presence of asymmetric carbon atom at the position marked by *2 in the compound of formula (A), the stereochemical integrity can be retained in the compound of formula (XI). Furthermore, where the compound of formula (XII) is optically active, owing to the presence of an asymmetric carbon atom at the position marked by *1 in formula (A), the stereochemical integrity at the asymmetric carbon atoms *1 and *2 can be retained in the compound of formula (I).

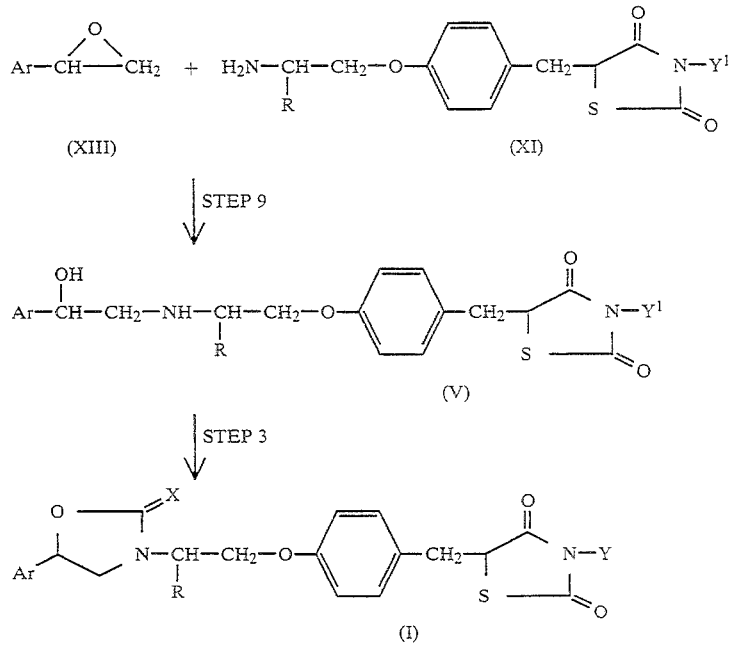

METHOD 3

In the above formulae, Ar, R, X and $Y^1$ are as defined above.

Step 9

A compound of formula (V) may be prepared by reacting an epoxy compound of formula (XIII) with an amino compound of formula (XI).

The reaction may, if desired, be carried out in the presence of an acid catalyst. Alternatively, the reaction may be carried out without a catalyst. Whilst the exact nature of the catalyst is not critical to the present invention, we have found that catalysts such as inorganic, for example mineral acids, e.g. hydrogen chloride and sulfuric acid; as well as Lewis acids, e.g. boron trifluoride, aluminum chloride; as well as basic alumina, are particularly suitable. The reaction is normally and preferably carried out in the presence of a solvent. There is no particular restriction on the nature of the solvent to be employed, provided that it has no adverse effect upon the reaction or on the reagents, and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; alcohols, such as methanol, ethanol or isopropanol; sulfoxides, such as dimethyl sulfoxide; nitriles, such as acetonitrile; water; and a mixture of any two or more of these solvents. The reaction may be carried out over a wide range of temperatures, and the precise reaction temperature is not critical to the invention. In general, we find it convenient to carry out the reaction either whilst ice-cooling, or with some heating. The time required for the reaction may also vary widely, depending upon many factors, notably the reaction temperature and the nature of the reagents and of the solvent. However, provided that the reaction is effected under the preferred conditions outlined above, a period of from 1 hour to several days will usually suffice.

The reaction is preferably carried out in the presence of a solvent at a temperature of from 30° to 120° C., for a period of from 1 hour to 1 day.

The compound of formula (V) may then be converted into a compound of formula (I) by reaction with a carbonylating or thiocarbonylating agent in the same manner as is described in Step 3, above.

Where the compounds of formula (XI) and (XIII) are optically active compounds, owing to the presence of asymmetric carbon atoms at the positions marked by *1 and *2 in the compound of formula (A), the stereochemical integrity can be retained in the compound of formula (I).

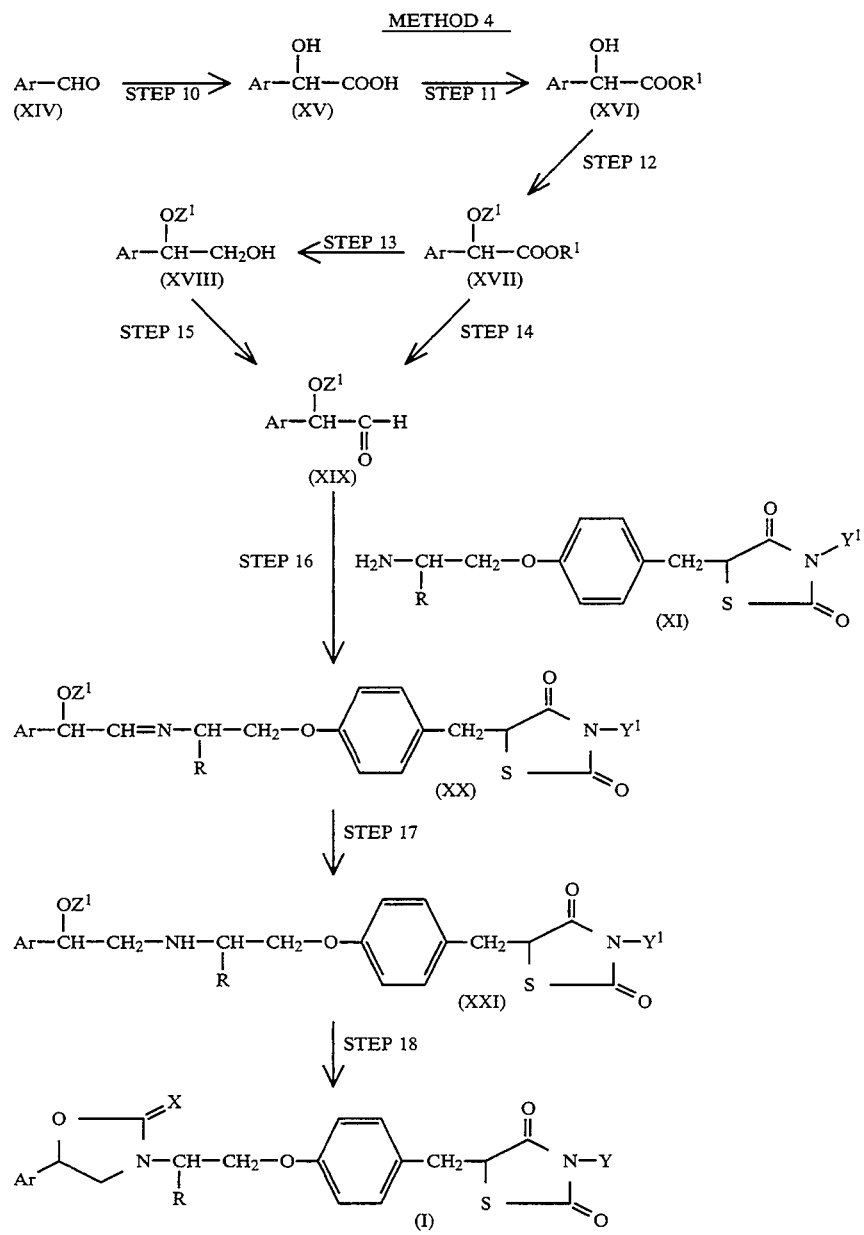

In the above formulae, Ar, R, X, Y and $Y^1$ are as defined above, $R^1$ represents a lower alkyl group, such as a methyl or ethyl group; $Z^1$ represents a hydrogen atom or a hydroxy-protecting group, such as a heterocyclic group, for example a tetrahydropyranyl or tetrahydrofuranyl group; an alkoxyalkyl group in which the alkoxy and alkyl parts each have from 1 to 4 carbon atoms, for example a methoxymethyl, 1-methoxyethyl, 1-ethoxypropyl, 1-methoxypropyl or 1-methoxybutyl group; an aralkyl group which may be as defined and exemplified above in relation to the ester groups, particularly the benzyl, diphenylmethyl and triphenylmethyl groups; a tri-substituted silyl group in which the substituents are three alkyl groups, which may be the same or different, each having from 1 to 4 carbon atoms, or 1 or 2 such alkyl groups and correspondingly 2 or 1 phenyl groups, for example the trimethylsilyl, t-butyldimethylsilyl or t-butyldiphenylsilyl groups.

Step 10

A compound of formula (XV) can be prepared by conventional procedures from a compound of formula (XIV), for example by following the procedure described in Organic Synthesis, I, 336, the disclosure of which is incorporated herein by reference.

The reaction may be carried out by reacting a compound of formula (XIV) with hydrogen cyanide or with a combination of trimethylsilyl cyanide and zinc iodide to produce a cyanohydrin compound, followed by acid-catalyzed hydrolysis. Although the first part of this reaction can be carried out over a wide range of temperatures, we generally prefer to effect the reaction whilst ice-cooling or with some heating. More preferably, however, the reaction is carried out at a temperature between room temperature and 100° C. The time required for the reaction may also vary, depending on, for example, the reaction temperature and the nature of the reagents. However, provided that the reaction is effected under the preferred conditions outlined above, a period of from 30 minutes to one day, preferably from one hour to ten hours, will usually suffice. The acid-catalyzed hydrolysis forming the second part of Step 10 is normally carried out using an acid, the exact nature of which is not critical to the present invention. Examples of suitable acids include: inorganic acids, such as hydrogen chloride or sulfuric acid; and organic acids, such as p-toluenesulfonic acid or acetic acid. The reaction is suitably carried out in the presence of an excess of water and, although the precise reaction temperature is not essential to the present invention, we find it convenient to effect the reaction at between room temperature and the reflux temperature of the reaction mixture, preferably whilst heating under reflux. The time required for the reaction may also vary widely and is dependent on many factors, notably the reaction temperature and the nature of the reagents. However, when following the preferred conditions outlined above, a period of from several tens of minutes to several tens of hours, particularly from 30 minutes to 10 hours, will normally suffice.

The reaction is preferably carried out whilst heating under reflux, in the presence of hydrogen chloride or sulfuric acid for a period of from 30 minutes to 10 hours.

Step 11

This step involves the preparation of a compound of formula (XVI) by esterification of a compound of formula (XV).

Esterification of a compound of formula (XV) may be peformed using any conventional technique. We have found that esterification with, for example, an acid catalyst, or an esterifying agent, such as a diazoalkane, or a combination of a halogenated alkyl compound with an alkali is particularly suitable.

Acid-catalyzed esterification may be effected by reacting the compound of formula (XV) with, for example, an excess of an alcohol, in the presence or absence of a solvent, and preferably in the presence of an inorganic acid, such as hydrogen chloride or sulfuric acid, or an organic acid, such as p-toluenesulfonic acid, at a suitable temperature, for example from room temperature to heating, for a suitable period, for example from several hours to several days.

Esterification using a diazoalkane is preferably effected in the presence of a solvent, for example: an alcohol, such as methanol or ethanol; a hydrocarbon, which may be aliphatic or aromatic, such as benzene, toluene, xylene, hexane or heptane; an ether, such as diethyl ether, tetrahydrofuran or dioxane; or a mixture of any two or more of the solvents described above. The reaction can take place over a wide range of temperatures, and the precise reaction temperature is not critical to the invention. In general, we find it convenient to carry out the reaction at a temperature of from ice-cooling to heating, more preferably at a temperature of from ice-cooling to 60° C. The time required for the reaction may also vary widely, depending on many factors, notably the reaction temperature and the nature of the reagents and solvent employed.

In an esterification reaction using an alkali and an alkyl halide, examples of the alkali which may be used include alkali metal carbonates, such as potassium carbonate or sodium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as diethyl ether, tetrahydrofuran or dioxane; hydrocarbons, such as benzene, toluene, xylene, hexane or heptane; amides, such as dimethylformamide, dimethylacetamide or hexamethylphosphoric triamide; and mixtures of any two or more of the solvents described above. The reaction can take place over a wide range of temperatures, and the precise reaction temperature is not critical to the invention. In general, we find it convenient to carry out the reaction at a temperature of from about room temperature to some heating. The time required for the reaction may also vary widely, depending on many factors, notably the reaction temperature and the nature of the reagents and solvent employed. However, provided that the reaction is effected under the preferred conditions outlined above, a period of from several hours to several days will usually suffice.

Step 12

The hydroxy group of the compound of formula (XVI) thus obtained is protected using a conventional hydroxy-protecting group to produce a compound of formula (XVII). Examples of the hydroxy-protecting groups which may be used include: tetrahydropyranyl, methoxymethyl, diphenylmethyl, trityl, trimethylsilyl, t-butyldimethylsilyl and t-butyldiphenylsilyl groups, for example, as described in T. W. Green, "Protective Groups in Organic Synthesis", John Wiley & Sons; and J. F. W. McOmie, "Protective Groups in Organic Chemistry", Plenum Press. This reaction may be effected using the procedure described by Green.

Step 13

A compound of formula (XVIII) can be prepared by reducing a compound of formula (XVII). The reaction is suitably carried out by contacting a compound of formula (XVII) with an appropriate reducing agent. Examples of suitable reducing agents include metal hydrides, such as lithium aluminum hydride or diisobutylaluminum hydride. The amount of reducing agent is not critical to the reaction, although, for economy, it is preferred that the amount should be at least equimolar with respect to the compound of formula (XVII). In general the reaction is normally carried out using from 1 to 50 moles, and preferably a large excess, of the reducing agent, per mole of the compound of formula (XVII). The reaction is normally and preferably carried out in the presence of a solvent. There is no particular restriction on the nature of the solvent to be employed, provided that it has no adverse effect upon the reaction or on the reagents involved, and that it can dissolve the reagents, at least to some extent. Examples of suitable solvents include ethers, such as diethyl ether, tetrahydrofuran and dioxane; and hydrocarbons, such as benzene, toluene, xylene, hexane and heptane. The reaction can take place over a wide range of temperatures, and the precise reaction temperature is not critical to the invention. In general, we find it convenient to carry out the reaction at a temperature of from about −60° C. to 50° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours will usually suffice.

Step 14

A compound of formula (XIX) may be prepared from a compound of formula (XVII) in a conventional manner, for example by reacting with diisobutylaluminum hydride in a solvent, typically a hydrocarbon solvent, such as hexane, heptane, benzene, toluene or xylene. The reaction may proceed over a wide range of temperatures, and the precise reaction temperature is not critical to the present invention. In general, however, we find it convenient to effect the reaction whilst cooling the reaction mixture, for example in a dry ice/acetone bath, although the reaction my also proceed between −100° C. and 0° C. The time required for the reaction may also vary widely depending on, for example, the reaction temperature and the nature of the reagents and of the solvent involved. However, provided that the reaction is effected under the preferred conditions outlined above, a period of from 30 minutes to 24 hours, preferably from one hour to five hours, will usually suffice.

Step 15

A compound of formula (XIX) may be prepared by oxidizing a compound of formula (XVIII). The reaction is carried out by conventional oxidation, for example oxidation using a pyridine sulfur trioxide complex or chromium oxidizing reagents, or by following the Swern oxidation method described by Mancuso, Huang & Swern in J. Org. Chem., Vol 43, No. 12, (1978) 2480.

More particularly, we have found that the reaction proceeds adequately when using the oxidizing agent described by Swern et al, supra. The precise temperature at which the reaction is effected is not critical to the invention, and the reaction will proceed over a wide range of temperatures. In general, however, we find it convenient to effect the reaction at a temperature of from −100° C. to 100° C., preferably from −75° C. to 50° C. The time required for the reaction may also vary widely depending on, for example, the reaction temperature and the nature of the reagents and of the solvent involved. However, provided that the reaction is effected under the preferred conditions outlined above, a period of from 1 minute to 3 hours, preferably from 5 minutes to one hour, will usually suffice.

Step 16

A compound of formula (XX) may be prepared by reacting a carbonyl compound of formula (XIX) with an amino compound of formula (XI). The reaction may be carried out in the same manner as described in Step 1, above.

Step 17

A compound of formula (XXI) may be prepared by reducing a compound of formula (XX). The reaction my be carried out in the same manner as described in Step 2, above.

Step 18

When $Z^1$ in the compound of formula (XXI) represents a hydroxy-protecting group, a compound of formula (I) may be produced by first de-protecting the compound of formula (XXI), using conventional procedures, and then by reacting the resulting compound with a carbonylating or thiocarbonylating agent, as described in Step 3, above. The deprotection may be carried out using conventional techniques, for example by following the procedure described in T. W. Green, Protective Groups in Organic Synthesis, John Wiley & Sons; and J. F. W. McOmie, Protective Groups in Organic Chemistry, Plenum Press.

Where the compounds of formula (XIX) and (XI) are optically active compounds, owing to the presence of asymmetric carbon atoms at the positions marked by *1 and *2 in the compound of formula (A), the stereochemical integrity can be retained in the compound of formula (I).

Alternatively, racemic compounds of formula (XV) can, if desired, be resolved to produce the individual isomers, that is [(R)-(XV)] and [(S)-(XV)], using optically active amines commonly used for conventional optical resolution. Examples of such amines include: (+)- or (−)-ephedrine and (d)- or (l)-1-phenylethylamine.

METHOD 5

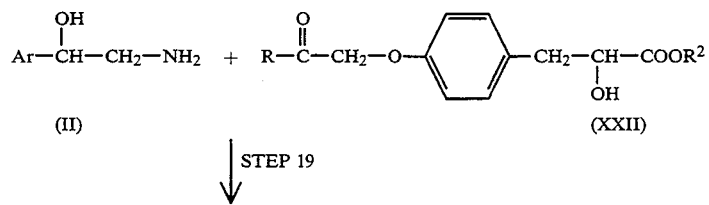

METHOD 5

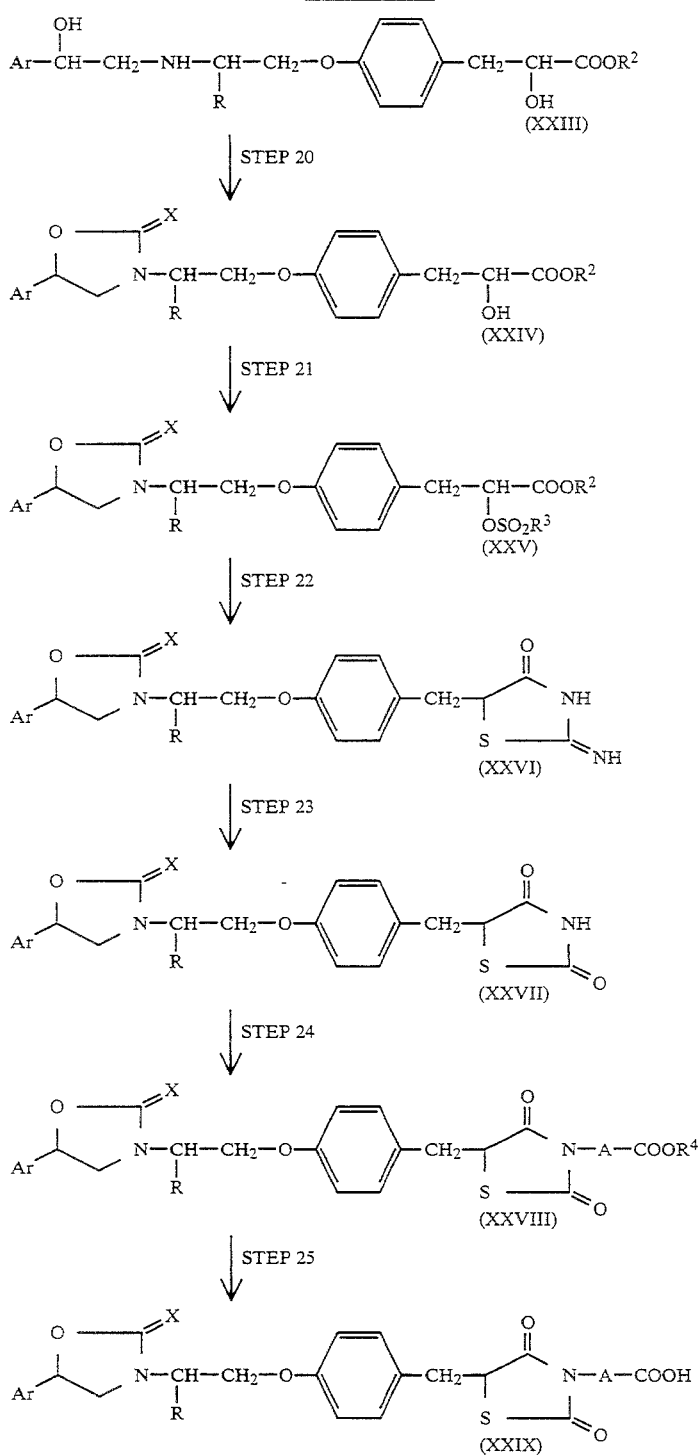

In the above formulae, Ar, R, X and A are as defined above, $R^2$ represents a $C_1$-$C_5$ alkyl group, such as a methyl or ethyl group; $R^3$ represents a $C_6$-$C_{10}$ aryl group, such as phenyl, p-tolyl or naphthyl group; a $C_6$-$C_{10}$ aryl group which has at least one substituent selected from the group consisting of substituents (a), as defined and exemplified above, for example a p-bromophenyl, 2-methoxyphenyl or 3-methylphenyl group; an unsubstituted $C_1$-$C_5$ alkyl group, such as a methyl or ethyl group; or a $C_1$-$_5$alkyl group which has at least one halogen substituent, for example a trifluoromethyl group; and $R^4$ represents an ester residue, as hereinabove defined.

Step 19

A compound of formula (XXIII) may be prepared by reacting a compound of formula (II) with a compound of formula (XXII) and reducing the resulting compound, following the procedure described in Steps 1 and 2, above.

Step 20

A compound of formula (XXIV) may be prepared by treating a compound of formula (XXIII) with a carbonylating or thiocarbonylating agent, following the procedure described in Step 3, above.

Step 21

A compound of formula (XXV) may be prepared by reacting a compound of formula (XXIV) with a sulfonylating agent in the presence of a base to remove any acid formed during the reaction.

There is no particular restriction on the nature of the sulfonylating agent employed in this reaction. Examples of suitable sulfonylating agents include: an arylsulfonyl chloride, such as a benzenesulfonyl chloride, p-toluenesulfonyl chloride or naphthalenesulfonyl chloride group; an arylsulfonyl chloride which has at least one halogen substituent, such as a p-bromobenzenesulfonyl chloride group; an unsubstituted $C_1$-$C_5$ alkanesulfonyl chloride, such as a methanesulfonyl chloride, ethanesulfonyl chloride, butanesulfonyl chloride group; or an alkanesulfonyl chloride group which has at least one halogen substituent, such as a trifluoromethanesulfonyl chloride group; and an unsubstituted $C_1$-$C_5$ alkanesulfonic anhydride, such as methanesulfonic anhydride; or substituted $C_1$-$C_5$ alkanesulfonic anhydride, such as a trifluoromethanesulfonic anhydride group. The exact nature of the base employed in this reaction is also not critical to the present invention, provided that it can remove any acid formed during the reaction. Examples of suitable bases include: organic bases, such as triethylamine, diisopropylethylamine or pyridine; and inorganic bases, particularly alkali metal carbonates, such as sodium carbonate or potassium carbonate. The reaction is normally carried out in the presence of a solvent. There is no particular restriction on the nature of the solvent to be employed, provided that it has no adverse effect upon the reaction or on the reagents involved, and that it can dissolve the reagents at least to some extent. Examples of suitable solvents include: hydrocarbons, either aromatic or aliphatic, such as benzene, toluene, xylene, hexane or heptane; halogenated hydrocarbons, such as chloroform, methylene chloride, 1,2-dichloroethane or carbon tetrachloride; ethers, such as diethyl ether, tetrahydrofuran or dioxane; amides, such as dimethylformamide, dimethylacetamide or hexamethylphosphoric triamide; nitriles, such as acetonitrile or propionitrile; sulfoxides, such as dimethyl sulfoxide; or a mixture of any two or more of the above solvents. The reaction will take place over a wide range of temperatures, and the precise reaction temperature is not critical to the present invention. In general, we find it convenient to effect the reaction whilst cooling or with some heating, preferably at a temperature of from ice-cooling to 50° C. The time required for the reaction also varies widely, depending on many factors, notably the reaction temperature and the nature of the reagents and of the solvent. However, provided that the reaction is effected under the preferred conditions outlined above, a period of from 30 minutes to 1 day, particularly from 1 to 15 hours, will usually suffice.

The reaction is preferably carried out using an ether, halogenated hydrocarbon, nitrile or amide as a solvent, at a temperature between ice-cooling and 50° C. and for a period of from 1 to 15 hours. More preferably the reaction is carried out in tetrahydrofuran, methylene chloride or acetonitrile at a temperature between ice-cooling and room temperature.

Step 22

A compound of formula (XXVI) may be prepared by reacting a compound of formula (XXV) with thiourea. The exact amount of thiourea used in this reaction is not essential to the present invention, although it is preferred that the thiourea should be present in excess with respect to the compound of formula (XXV), preferably that the thiourea should be present in an amount at least 1.2 to 5 times, and most preferably from 1.5 to 3 times the amount of the compound of formula (XXV). The reaction is normally and preferably carried out in the presence of a solvent. There is no particular restriction on the nature of the solvent to be employed, provided that it has no adverse effect upon the reaction or on the reagents involved, and that it can dissolve the reagents, at least to some extent. Examples of suitable solvents include: alcohols, such as methanol, ethanol or ethylene glycol monomethyl ether; amides, such as dimethylformamide, dimethylacetamide or hexamethylphosphoric triamide; sulfoxides, such as dimethyl sulfoxide; sulfolane; or a mixture of any two or more of these solvents. The reaction may be carried out over a wide range of temperatures, and the precise reaction temperature is not critical to the invention. In general, however, we find it convenient to effect the reaction at a temperature between room temperature and the reflux temperature of the reaction mixture, preferably by heating under reflux The time required for the reaction also varies, depending on many factors, notably the reaction temperature and the nature of the reagents and of the solvent. However, provided that the reaction is effected under the preferred conditions outlined above, a period of from 30 minutes to 20 hours, particularly from 1 to 5 hours, will usually suffice.

The reaction is preferably carried out by heating in ethylene glycol monomethyl ether under reflux for from 1 to 5 hours.

Step 23

A compound of formula (XXVII) may be prepared by hydrolyzing a compound of the formula (XXVI), preferably in the presence of an acid catalyst. This hydrolysis may take place directly after preparation of the compound of formula (XXVI) and without isolation of that compound or after isolation of the compound, for example as described hereinafter.

The exact nature of the catalyst is not essential to the present invention. Examples of suitable catalysts include: inorganic acids, such as hydrogen chloride, hydrogen bromide, phosphoric acid or sulfuric acid; and organic acids such as p-toluenesulfonic acid, methanesulfonic acid, trifluoromethanesulfonic acid or trifluoroacetic acid. Where this hydrolysis is carried out without isolation of the compound of formula (XXVI), the reaction is preferably carried out in the presence of a large excess of water per mole of the thiourea used in Step 22. Where this hydrolysis is performed on a compound of formula (XXVI) which has been isolated, the reaction is preferably carried out in the presence of a large excess of water per mole of the compound of formula (XXVI). The reaction is normally and preferably carried out in the presence of a solvent. There is no particular restriction on the nature of the solvent used, provided that it has no adverse effect upon the reaction or on the reagents involved, and that it can dissolve the reagents, at least to some extent. Examples of suitable solvents include: alcohols, such as methanol, ethanol or ethylene glycol monomethyl ether; amides, such as dimethylformamide, dimethylacetamide or hexamethylphosphoric triamide; sulfoxides, such as dimethyl sulfoxide; sulfolane; or a mixture of any two or more of the above solvents. The reaction may be carried out over a wide range of temperatures, and the precise reaction temperature is not critical to the invention. In general, we find it convenient to effect the reaction whilst heating under reflux. The time required for the reaction also varies widely, depending on many factors, notably the reaction temperature and the nature of the reagents and of the solvent. However, provided that the reaction is effected under the preferred conditions outlined above, a period of from 30 minutes to 10 hours, particularly from 1 to 5 hours, will usually suffice.

The reaction is preferably carried out by heating in ethylene glycol monomethyl ether under reflux, for a period of from 1 to 5 hours.

Step 24

A compound of formula (XXVIII) may be prepared by converting a compound of the formula (XXVII) to a salt, preferably an alkali metal salt, such as a sodium or potassium salt, followed by reaction with a compound of formula: V—A—COOR$^4$ (wherein V, A and R$^4$ are as defined above).

Each of these two reactions is preferably carried out in the presence of a solvent. There is no particular restriction on the nature of the solvent to be employed, provided that it has no adverse effect upon the reaction or on the reagents involved, and that it can dissolve the reagents, at least to some extent. Examples of suitable solvents include: amides, such as dimethylformamide, dimethylacetamide or hexamethylphosphoric triamide; urea derivatives, such as N,N'-dimethylimidazolidinone; sulfoxides, such as dimethyl sulfoxide; sulfolane; or a mixture of any two or more of these solvents. The exact nature of the salifying agent in the first part of this step is not essential to the invention. Examples of suitable reagents include: sodium hydride, potassium hydride, sodium methoxide, sodium ethoxide and potassium t-butoxide. The reaction may take place over a wide range of temperatures and the precise reaction temperature is not critical to the invention. In general, we find it convenient to effect the reaction at a temperature between ice-cooling or upon some heating, preferably at a temperature between ice-cooling and room temperature. The time required for the reaction also varies, depending on many factors, including the reaction temperature and the nature of the reagents and of the solvent. However, provided that the reaction is effected under the preferred conditions outlined above, a period of from 30 minutes to 10 hours, preferably from 1 to 6 hours, will usually suffice.

It is preferred that the first part of this complete reaction is carried out using sodium hydride in an amide as solvent, at a temperature between ice-cooling and room temperature and for a period of from 1 to 6 hours.

The alkali metal salt obtained as a result of this procedure is then preferably reacted, without first being isolated from the above reaction mixture, with a compound of formula V—A—COOR$^4$ (wherein V, A and R$^4$ are as defined above) for a period of from 1 to 6 hours, whilst ice-cooling or with some heating. More preferably this reaction is effected at a temperature between ice-cooling and room temperature.

Step 25

A compound of formula (XXIX) may be prepared by hydrolyzing a compound of formula (XXVIII). This reaction may be effected using conventional techniques for the hydrolysis of a carboxylic acid ester, for example in the presence of water and an acid or base catalyst.

Where the reaction is effected in the presence of an acid catalyst, there is no particular restriction on the nature of the acid catalyst to be employed, provided that it has no adverse effect upon the reaction. Examples of suitable acids include: inorganic acids, such as hydrogen chloride, sulfuric acid, phosphoric acid and hydrogen bromide. Where the reaction is effected in the presence of a base catalyst, there is no particular restriction on the nature of the base catalyst to be employed, provided that it has no adverse effect upon the reaction. Examples of suitable bases include: alkali metal carbonates, such as sodium carbonate or potassium carbonate; alkali metal hydroxides, such as sodium hydroxide or potassium hydroxide; or a concentrated solution of ammonia in methanol. The hydrolysis is preferably carried out in the presence of a solvent. There is no particular restriction on the nature of the solvent to be employed, provided that it has no adverse effect on the reaction or on the reagents, and that it can dissolve the reagents, at least to some extent. Solvents which are conventionally used in such hydrolysis reactions may equally be employed in this reaction. Examples of suitable solvents include: water; alcohols, such as methanol, ethanol or propanol; ethers, such as tetrahydrofuran or dioxane; or a mixture of one or more of these solvents with water.

The reaction my take place over a wide range of temperatures and the precise reaction temperature is not critical to the present invention. In general, we find it convenient to effect the reaction at a temperature of from 0° C. to 150° C. The time required for the reaction may also vary widely, depending on many factors, such as the reaction temperature and the nature of the reagents and of the solvent. However, provided that the reaction is effected under the preferred conditions outlined above, a period of from 1 to 10 hours will usually suffice.

After completion of any of the reactions described above the desired compounds can be recovered from the reaction mixture by conventional means. For example, one suitable recovery procedure comprises extracting the compound from the reaction mixture by adding a suitable solvent; and freeing the extracts from the solvent by distillation. The resulting product can then, if desired, be further purified by conventional means, for example recrystallization, reprecipitation or the various chromatography techniques, notably column chromatography, preferably through silica gel.

BIOLOGICAL ACTIVITY

The compounds of formula (I) and their pharmaceutically acceptable salts and esters have a variety of valuable physiological activities, which render them of great potential for the treatment or prophylaxis of a variety of physiological disorders. For example, they improve hyperglycemia, increase glucose tolerance, they inhibit the activity of aldose reductase, and they improve hepatic gluconeogenesis and hyperlipemia; they are useful as preventive and/or therapeutic agents for hyperglycemia, obesity, hyperlipemia and such diabetic complications as retinopathy, nephropathy, neuropathy, cataracts, coronary heart disease and arteriosclerosis; they are also useful for the treatment and prevention of obesity-related hypertension and osteoporosis. In addition, since the compounds of the present invention have a very low toxicity, they are useful as a preventive and/or therapeutic agents for the diseases and disorders mentioned above.

The biological activities of the compounds of the present invention are illustrated in the following Experiments, in which the compounds of the invention are identified by the number of the one of the following Examples in which its preparation is described.

EXPERIMENT 1

Ability of the Compounds to Lower Blood Sugar Levels

The ability of the compounds of the present invention to lower blood sugar levels in mice was measured as follows.

Hyperglycemic male KK mice, each weighing more than 40 g, were each administered 50 mg/Kg of the compound to be tested in a 1:1 by volume mixture of polyethylene glycol 400 and 0.5% w/v carboxymethylcellulose in an aqueous sodium chloride solution, and then allowed to stand for 18 hours with unlimited food. At the end of this time blood samples were taken from the tail. Blood sugar levels (BSL) were determined by means of a glucose analyzer (GL-101, a product of Mitsubishi Kasei, Co.). The rate (R) at which the test compound lowered the blood sugar levels was calculated according to the following equation:

$$R\% = \left[ \frac{(B - A)}{B} \right] \times 100$$

where

B: Blood sugar level in the group administered a solvent

A: Blood sugar level in the group administered a test sample.

The results are shown in Table 3.

TABLE 3

| Compound of Example No. | R(%) |
|---|---|
| Fraction 1 of Example 1 | 12.5 |
| Fraction 1 of Example 2 | 31.1 |
| Fraction 2 of Example 2 | 32.4 |
| Fraction 1 of Example 3 | 17.6 |
| Fraction 2 of Example 3 | 34.0 |
| Example 4 | 2.6 |
| Example 6 | 39.8 |
| Example 7 | 23.0 |
| Example 10 | 25.4 |
| Control* | −13.7 |

The control compound is 3-{2-[4-(2,4-dioxothiazolidin-5-ylmethyl)phenoxy]ethyl}-5-(3-chlorophenyl)oxazolidin-2-one.

As is clearly shown in Table 3, all of the compounds tested had good activity in reducing the blood sugar levels.

EXPERIMENT 2

Hypoglycemic effect during glucose load

The hypoglycemic effect of the compounds of the present invention during glucose load in mice was measured as follows.

Three month old KK male mice, each weighing 28 to 30 g, were fasted overnight, and then 1 mg/kg or 10 mg/Kg of the compound to be tested in carboxymethylcelluose (CMC) or carboxymethylcellulose as a control were administered orally. After 60 minutes, 1.2 g/kg of D-glucose was administered subcutaneously. Then, at 60 and 120 minutes after the subcutaneous glucose injection, blood samples were taken, and the glucose levels were determined by means of a glucose analyzer (GL-101, a product of Mitsubishi Kasei, Co.). The hypoglycemic rates (R) of the test compound during the glucose load were calculated according to the following equation:

$$R = [1 - (B/A)] \times 100$$

where

A: Blood glucose level in the group administered CMC

B: Blood glucose level in the group administered a test sample.

The results are shown in Table 4.

TABLE 4

| Compound of Example No. | Dose (mg/kg) | Mice (No.) | R (%) 60 min. | R (%) 120 min. |
|---|---|---|---|---|
| Fraction 1 of Ex. 1 | 1 | 3 | 12.5 | −0.1 |
| Fraction 2 of Ex. 1 | 1 | 3 | 22.5 | 21.7 |
| Fraction 1 of Ex. 2 | 1 | 3 | 15.1 | 14.9 |
| Fraction 2 of Ex. 2 | 1 | 3 | 27.4 | 21.3 |
| Fraction 1 of Ex. 3 | 10 | 3 | 30.7 | 27.0 |
| Fraction 2 of Ex. 3 | 1 | 3 | 14.4 | 23.6 |
| Example 5 | 1 | 3 | 16.9 | 15.4 |
| Example 6 | 1 | 3 | 30.0 | 32.6 |
| Example 7 | 1 | 3 | 24.3 | 30.9 |
| Example 9 | 1 | 3 | 11.9 | 20.8 |
| Control | 1 | 3 | 5.2 | 1.7 |

The control compound is 3 - {2 - [4 -(2,4-dioxothiazolidin-5-ylmethyl)phenoxy]ethyl}-5-(3-chlorophenyl)oxazolidin-2-one.

As is clearly shown in Table 4, all of the tested compounds showed an excellent hypoglycemic effect.

EXPERIMENT 3

Toxicity

The toxicity of the compounds of the present invention was tested on male ddY mice, divided into groups of 3. The test compound was administered orally to each test animal at a dose of 300 mg/Kg of body weight. The test compounds used were fractions 1 and 2 of Example 1, and the compounds of Examples 6, 7 and 10. The animals were observed for a period of one week after administration and, during that period, they showed no abnormalities which could be attributed to the test compounds. All of the animals were still alive at the end of the period of observation.

In view of the substantial dose adminstered to each animal, the zero mortality rate indicates that the compounds of the present invention have very low toxicity.

The compounds of the present invention can be administered in various forms, depending upon the patient and the desired route of administration. Suitable formulations for oral administration include tablets, capsules, granules, powders or syrups; and suitable formulations for parenteral administration include injections (which may be intravenous, intramuscular or subcutaneous), drops or suppositories. These various preparations can be prepared by conventional means in which the active compound is mixed with any known additives commonly employed in the field of pharmaceutical preparations, such as vehicles, binders, disintegrators, lubricants, corrigents, solubilizers, suspending agents and coating agents. The dosage may be varied depending on the symptoms, age and body weight of the patient, the route of administration and the form of the preparation. However, a daily dose of from 0.01 mg to 2,000 mg, which may be administered in a single dose or in divided doses, is usually appropriate for an adult human patient.

The preparation of the compounds of the present invention is further illustrated by the following non-limiting Examples, and the preparation of certain of the starting materials is shown in the subsequent Preparations.

EXAMPLE 1

3-{2-[4-(2,4-Dioxothiazolidin-5-ylmethyl)phenoxy]-1-methylethyl}-5-(3-Chlorophenyl)oxazolidin-2-one

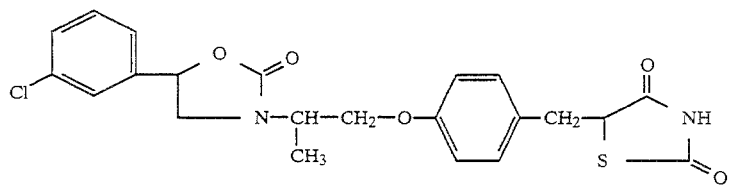

360 mg of carbonyldiimidazole were added to a solution of 640 mg of 5-(4-{2-[2-(3-chlorophenyl)-2-hydroxyethylamino]propoxy}benzyl)thiazolidine-2,4-dione ½ ethyl acetate [prepared as described in Preparation 10] in 5 ml of dimethylformamide, and the mixture was allowed to stand overnight at room temperature. At the end of this time, the reaction mixture was diluted with a saturated aqueous solution of sodium chloride and then extracted with ethyl acetate. The extract was then washed three times with a saturated aqueous solution of sodium chloride, after which it was dried over anhydrous sodium sulfate. The ethyl acetate was then removed from the dried extract by distillation under reduced pressure, and the residue obtained was purified by column chromatography through silica gel, using a 5:4 by volume mixture of hexane and ethyl acetate as the eluent, to give the title compound. The title compound was produced in the form of two isomeric mixtures which eluted separately from the column: (i) the first fraction consisting of 150 mg of a mixture of isomers having the (R,S)- and the (S,R)-configuration at the asymmetric carbon atoms marked respectively by *1 and *2 in formula (A), above, the mixture melting at between 56° C. and 59° C.; and (ii) the second fraction consisting of 150 mg of a mixture of isomers having the (R,R)- and the (S,S)-configuration at the asymmetric carbon atoms marked respectively by *1 and *2 in formula (A), above, the mixture melting at between 58° C. and 66° C.

EXAMPLE 2

3-{2-[4-(2,4-Dioxothiazolidin-5-ylmethyl)phenoxy]-1-methylethyl}-5-(3-chlorophenyl)oxazolidine-2-thione

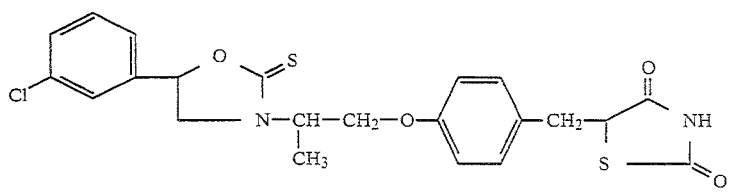

A procedure similar to that described in Example 1, above, was followed, but using 0.41 g of thiocarbonyldiimidazole and 1.0 g of 5-(4-{2-[2-(3-chlorophenyl)-2-hydroxyethylamino]propoxy}benzyl)thiazolidine-2,4-dione ½ ethyl acetate [prepared as described in Preparation 10] in a mixture of 2 ml of dimethylformamide and 2 ml of methylene chloride. The crude product thus obtained was purified by column chromatography through silica gel, using a 1:1 by volume mixture of hexane and ethyl acetate as the eluent, to obtain the title compound in the form of a mixture of isomers, which eluted separately from the column: (i) the first fraction consisting of 0.2 g of a mixture of isomers having the (R,R)- and the (S,S)-configuration at the asymmetric carbon atoms marked respectively by *1 and *2 in formula (A), above, the mixture having an Rf (rate of flow)=0.56 (thin layer chromatography on silica gel, using a 2:3 by volume mixture of hexane and ethyl acetate as the developing solvent); and (ii) the second fraction consisting of 0.2 g of a mixture of isomers having the (R,R)- and the (S,S)-configuration at the asymmetric carbon atoms marked respectively by *1 and *2 in formula (A), above, the mixture having an Rf=0.47 (thin layer chromatography on silica gel, using a 2:3 by volume mixture of hexane and ethyl acetate as the developing solvent).

EXAMPLE 3

3-{2-[4-(3-Methoxycarbonylmethyl-2,4-dioxothiazolidin-5-ylmethyl)phenoxy]-1-methylethyl}-5-(3-chlorophenyl)oxazolidin-2-one

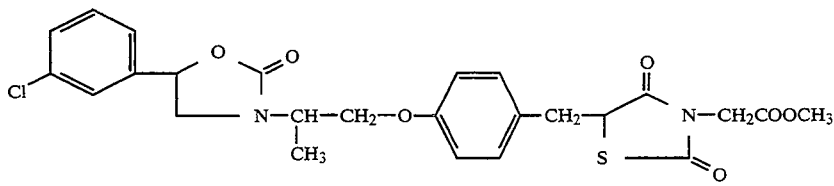

0.094 g of a 55% w/w dispersion of sodium hydride in mineral oil was added to a solution of 0.9 g of 3-{2-[4-(2,4-dioxothiazolidin-5-ylmethyl)phenoxy]-1-methylethyl}-5-(3-chlorophenyl)oxazolidin-2-one [prepared as described in Example 1, above] in 15 ml of dimethylformamide, and the mixture was stirred at room temperature for one hour. At the end of this time, 1.3 g of methyl bromoacetate were slowly added, whilst ice-cooling. The reaction mixture was then allowed to stand at room temperature for 3 days, after which it was worked up using a procedure similar to that described in Example 1, above. The product thus obtained in crude form was purified by column chromatography through silica gel, using a 1:1 by volume mixture of hexane and ethyl acetate as the eluent, to obtain the title compound as a mixture of isomers, which eluted separately from the column: (i) the first fraction consisting of 0.35 g of a mixture of isomers having the (R,S)- and the (S,R)-configuration at the asymmetric carbon atoms marked respectively by *1 and *2 in formula (A), above, the mixture having an Rf=0.56 (thin layer chromatography on silica gel, using a 2:3 by volume mixture of hexane and ethyl acetate as the developing solvent); and (ii) the second fraction consisting of 0.3 g of a mixture of isomers having the (R,R)- and the (S,S)-configuration at the asymmetric carbon atoms marked respectively by *1 and *2 in formula (A), above, the mixture having an Rf=0.35 (thin layer chromatography on silica gel, using a 2:3 by volume mixture of hexane and ethyl acetate as the developing solvent).

EXAMPLE 4

3-{2-[4-(2,4-Dioxothiazolidin-5-ylmethyl)phenoxy]-1-methylethyl}-5-(2-naphthyl)oxazolidine-2-thione

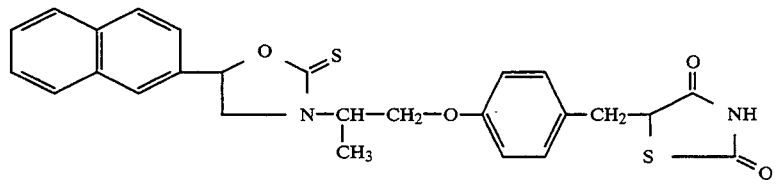

A procedure similar to that described in Example 1, above, was followed, but using 390 mg of 5-(4-{2-[2-(2-naphthyl)-2-hydroxyethylamino]propoxy}benzyl)-thiazolidin-2,4-dione [prepared as described in Preparation 5], 20 ml of acetonitrile and 460 mg of thiocarbonyldiimidazole, to obtain the title compound in crude form. The crude product was then purified by column chromatography through silica gel, using a 1:1 by volume mixture of ethyl acetate and hexane as the eluent, to obtain 250 mg of the title compound, which softens at between 75° C. and 85° C.

EXAMPLE 5

3-{2-[4-(2,4-Dioxothiazolidin-5-ylmethyl)phenoxy]-1-methylethyl}-5-(2,5-dimethoxy-3,4,6-trimethylphenyl)oxazolidin-2-one

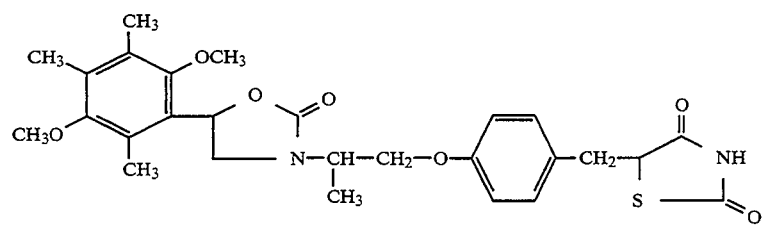

A procedure similar to that described in Example 1, above, was followed, but using 160 mg of 5-(4-{2-[2-(2,5-dimethoxy-3,4,6-trimethylphenyl)-2-hydroxyethylamino]-propoxy}benzyl)thiazolidine-2,4-dione [prepared as described in Preparation 1], 6 ml of methylene chloride and 192 mg of carbonyldiimidazole, to give the title compound in crude form. This crude product was purified by column chromatography through silica gel, using a 4:5 by volume mixture of hexane and ethyl acetate as the eluent, to give 48 mg of the title compound. The title compound eluted from the column in two fractions: (i) the first fraction consisting of a mixture of isomers having the (R,S)- and the (S,R)-configuration at the asymmetric carbon atoms marked respectively by *1 and *2 in formula (A), above, the mixture having an Rf=0.52 (thin layer chromatography on silica gel, using a 1:2 by volume mixture of hexane and ethyl acetate as the developing solvent); and (ii) the second fraction consisting of a mixture of isomers having the (R,R)- and the (S,S)-configuration at the asymmetric carbon atoms marked respectively by *1 and *2 in formula (A), above, the mixture having an Rf=0.44 (thin layer chromatography on silica gel, using a 1:2 by volume mixture of hexane and ethyl acetate as the developing solvent).

EXAMPLE 6

3-{2-[4-(2,4-Dioxothiazolidin-5-ylmethyl)phenoxy]-1(R)-methylethyl}-5(R)-(3-chlorophenyl)-oxazolidin-2-one

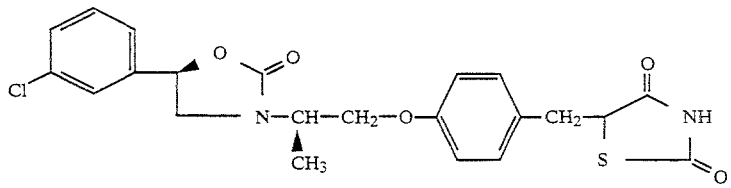

A procedure similar to that described in Example 1, above, was followed, but using 13 g of 5-(4-{2(R)-[2(R)-(3-chlorophenyl)-2-hydroxyethylamino]propoxy}benzyl)thiazolidine-2,4-dione [prepared as described in Preparation 4], 4.86 g of carbonyldiimidazole and 100 ml of dimethylformamide, to give 10.4 g of the title compound, melting at between 144° C. and 149° C.

[α]$_D^{23}$ +58.1° (c=1.000, chloroform).

EXAMPLE 7

3-{2-[4-(2,4-Dioxothiazolidin-5-ylmethyl)phenoxy]-1(R)-methylethyl}-5(R)-(3:chlorophenyl)-oxazolidine-2-thione

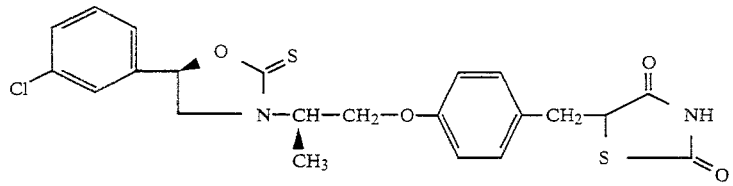

A procedure similar to that described in Example 1, above, was followed, but using 13 g of 5-(4-{2(R)-[2(R)-(3-chlorophenyl)-2-hydroxyethylamino]propoxy}benzyl)thiazolidine-2,4-dione [prepared as described in Preparation 4], 5.35 g of thiocarbonyldiimidazole and 100 ml of dimethylformamide, to give 10.56 g of the title compound, melting at between 164° C. and 173° C.

[α]$_D^{23}$ +25.6° (c=0.995, chloroform).

40.4 μl of a 28% w/w solution of sodium methylate in methanol were added to a mixture of 100 mg of the compound obtained above with 1 ml of methanol. The resulting mixture was stirred at room temperature for 5 minutes. At the end of this time, the methanol was removed by distillation under reduced pressure, and ethyl acetate was added to the residue to cause the formation of crystals. The resulting crystals were recovered by filtration and dried to give 100 mg of the sodium salt monohydrate of the title compound, melting at between 216° and 218° C.

EXAMPLE 8

3-{2-[4-(2,4-Dioxothiazolidin-5-ylmethyl)phenoxy]-1-methylethyl}-5-(3-trifluoromethylphenyl)-oxazolidine-2-thione

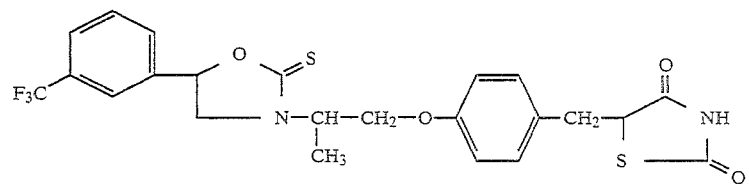

A procedure similar to that described in Example 1, above, was followed, but using 1.0 g of 5-(4-{2-[2(3-trifluoromethylphenyl)-2-hydroxyethylamino]propoxy}-benzyl)thiazolidine-2,4-dione [prepared as described in Preparation 6], 15 ml of dimethylformamide and 380 mg of thiocarbonyldiimidazole, to give the title compound in crude form. This crude product was purified by column chromatography through silica gel, using a 3:2 by volume mixture of hexane and ethyl acetate as the eluent, to obtain the title compound as a mixture of two isomers, which eluted separately from the column: (i) the first fraction to elute, consisting of 210 mg of a mixture of isomers having the (R,S)- and the (S,R)-configuration at the asymmetric carbon atoms marked respectively by *[1] and *[2] in formula (A), above, the mixture having an Rf=0.35 (thin layer chromatography on silica gel, using a 3:2 by volume mixture of hexane and ethyl acetate as the developing solvent); and (ii) the second fraction to elute, consisting of 180 mg of a mixture of isomers having the (R,R)- and the (S,S)-configuration at the asymmetric carbon atoms marked respectively by *[1] and *[2] in formula (A), above, the mixture having an Rf=0.25 (thin layer chromatography on silica gel, using a 3:2 by volume mixture of hexane and ethyl acetate as the developing solvent).

EXAMPLE 9

3-{2-[4-(3-Methoxycarbonylmethyl-2,4-dioxothiazolidin-5-ylmethyl)phenoxy]-1-(R)-methylethyl}-5(R)-3-chlorophenyl)oxazolidin-2-one

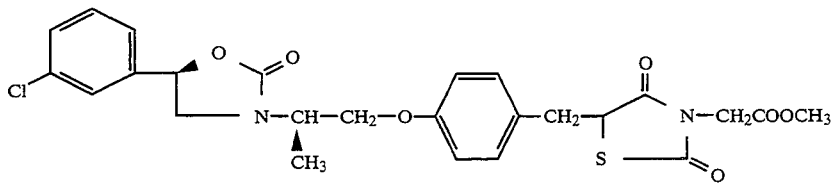

procedure similar to that described in Example 3, above, was followed, but using 2.0 g of 3-{2-[4-(2,4-dioxothiazol-5-ylmethyl)phenoxy]-1(R)-methylethyl}-5(R)-(3-chlorophenyl)oxazolidin-2-one [prepared as described in Example 6], 20 ml of dimethylformamide, 227 mg of a 55% w/w dispersion of sodium hydride in mineral oil and 0.6 ml of methyl bromoacetate, to give the title compound in crude form. This crude product was then purified by column chromatography through silica gel, using a 1:1 by volume mixture of ethyl acetate and hexane as the eluent, to give 1.87 g of the title compound, having an Rf=0.28 (thin layer chromatography on silica gel, using a 1:1 by volume mixture of ethyl acetate and hexane as the developing solvent).

$[\alpha]_D^{25}$ +6.5° (c=1,002, chloroform).

EXAMPLE 10

3-{2-[4-(3-Methoxycarbonylmethyl-2,4-dioxothiazolidin-5-ylmethyl) phenoxy]- 1(R)-methylethyl}-5(R)-(3-chlorophenyl)oxazolidine- 2-thione of the title compound, having an Rf=0.25 (thin layer chromatography on silica gel, using a 1:2 by volume mixture of ethyl acetate and hexane as the developing solvent).

$[\alpha]_D^{25}$ +28.2° (c=1.000, chloroform).

EXAMPLE 11

3-{2-[4-(3-t-Butoxycarbonylmethyl-2,4-dioxothiazolidin- 5-ylmethyl)phenoxy]-1(R)-methylethyl}-5(R)-(3-chlorophenyl)oxazolidine-2-thione

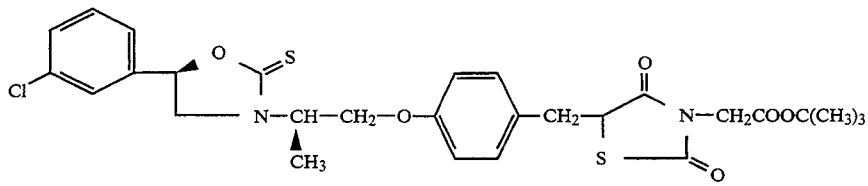

A procedure similar to that described in Example 3, above, was followed, but using 250 mg of 3-{2-[4-(2,4-dioxothiazolidin-5-ylmethyl)phenoxy]-1(R)-methylethyl}-5(R)-(3-chlorophenyl)oxazolidine-2-thione [prepared as described in Example 7], 10 ml of dimethylformamide, 23 mg of a 55% w/w dispersion of sodium hydride in mineral oil and 0,088 ml of t-butyl bromoacetate, to give the title compound in crude form. This crude product was then purified by column chromatography through silica gel, using a 1:2 by volume mixture

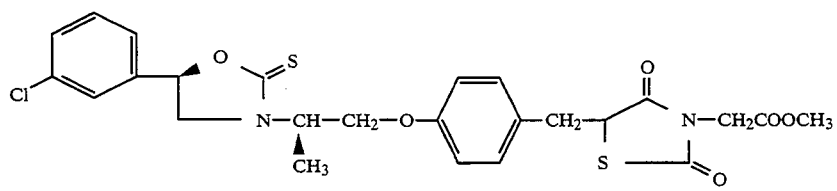

A procedure similar to that described in Example 3, above, was followed, but using 2.0 g of 3-{2-[4-(2,4-dioxothiazolidin-5-ylmethyl)phenoxy]-1(R)-methylethyl}5(R)-(3-chlorophenyl)oxazolidine-2-thione [prepared as described in Example 7], 20 ml of dimethylformamide, 220 mg of a 55% w/w dispersion of sodium hydride in mineral oil and 0.58 ml of methyl bromoacetate, to give the title compound in crude form. This crude product was then purified by column chromatography through silica gel, using a 1:2 by volume mixture of ethyl acetate and hexane as the eluent, to give 1.03 g of ethyl acetate and hexane as the eluent, to give 229 mg of the title compound, having an Rf=0.26 (thin layer chromatography on silica gel, using a 1:2 by volume mixture of ethyl acetate and hexane as the developing solvent).

EXAMPLE 12

3-{2-[4-(2,4-dioxothiazolidin-5-yl-methyl)phenoxy]-1(R)-isobutylethyl}-5(R)-(3-chlorophenyl)oxazolidin-2-one

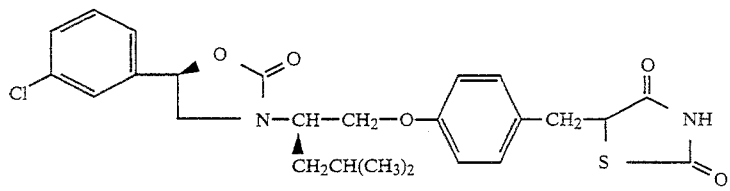

A procedure similar to that described in Example 1, above, was followed, but using 125 mg of 5-(4-{2(R)-[2(R)-(3-chlorophenyl)-2-hydroxyethylamino]-4-methylpentyloxy}benzyl)thiazolidine-2,4-dione [prepared as described in Preparation 19], 57.2 mg of carbonyldiimidazole and 10 ml of dimethylformamide, to give the title compound in crude form. This crude product was then purified by column chromatography through silica gel, using a 1:2 by volume mixture of ethyl acetate and hexane as the eluent, to give 105 mg of the title compound, having an Rf=0.46 (thin layer chromatography on silica gel, using a 1:1 by volume mixture of ethyl acetate and hexane as the developing solvent).

EXAMPLE 13

3-{2-[4-(2,4-dioxothiazolidin-5-yl-methyl)phenoxy]-1(R)-isobutylethyl}-5(R)-(3-chlorophenyl)oxazolidine-2-thione

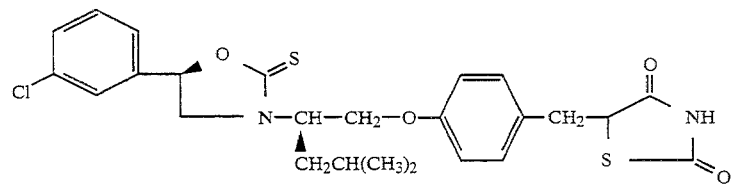

A procedure similar to that described in Example 1, above, was followed, but using 12 mg of 5-(4-{2(R)-[2(R)-(3-chlorophenyl)-2-hydroxyethylamino]-4-methylpentyloxy}benzyl)thiazolidine-2,4-dione [prepared as described in Preparation 19], 6.8 mg of thiocarbonyldiimidazole and 2 ml of dimethylformamide, to give the title compound in crude form. This crude product was then purified by thin layer chromatography on silica gel, using a 1:1 by volume mixture of ethyl acetate and hexane as the eluent, to give 11.9 mg of the title compound, having an Rf=0.54 (thin layer chromatography on silica gel, using a 1:1 by volume mixture of ethyl acetate and hexane as the developing solvent).

EXAMPLE 14

3-{2-[4-(3-ethoxycarbonylethyl-2,4-dioxothiazolidin-5-ylmethyl)phenoxy]-1(R)-methylethyl}-5(R)-(3-chlorophenyl)oxazolidine-2-thione

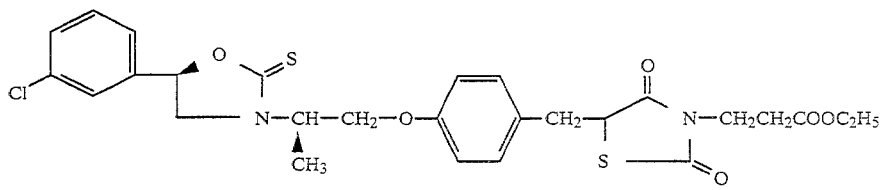

13 mg of a 55% w/w dispersion of sodium hydride in mineral oil was added to a solution of 150 mg of 3-{2-[4-(2,4-dioxothiazolidin-5-ylmethyl)phenoxy]-1(R)-methylethyl}-5(R)-(3-chlorophenyl)oxazolidine-2-thione [prepared as described in Example 7] in 10 ml of dimethylformamide, and the mixture was stirred at room temperature for one hour. At the end of this time, 0.04 ml of ethyl 3-bromopropionate were slowly added, whilst ice-cooling. The mixture was then stirred at room temperature for 4 hours, after which it was allowed to stand overnight at the same temperature. 0.22 g of potassium carbonate and 0.2 ml of ethyl 3-bromopropionate were then added and the mixture was heated at 60° C. for four hours. Water was then added to the reaction mixture, and the mixture was extracted with ethyl acetate. The resulting extract was then dried over anhydrous sodium sulfate and the solvent was removed by distillation under reduced pressure. The residue was then purified by column chromatography through silica gel, using a 1:2 by volume mixture of ethyl acetate and hexane as the eluent, to give 25 mg of the title compound, having an Rf=0.45 (thin layer chromatography on silica gel, using a 1:1 by volume mixture of ethyl acetate and hexane as the developing solvent).

EXAMPLE 15

3-{2-[4-(2,4-Dioxothiazolidin-5-ylmethyl)phenoxy]-1-methylethyl}-5-(3,5-dimethyl-4-hydroxyphenyl)oxazolidin-2-one

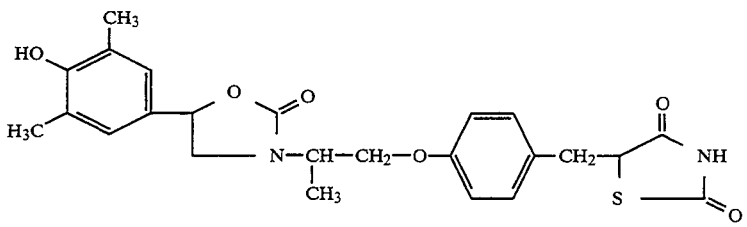

A procedure similar to that described in Example 1, above, was followed, but using 250 mg of 5-[4-{2-(2-[3,5-dimethyl-4-hydroxyphenyl]-2-hydroxyethylamino)propoxy}benzyl]thiazolidine-2,4 -dione [prepared as described in Preparation 22], 95 mg of carbonyldiimidazole and 3 ml of dimethylformamide, to obtain the title compound in crude form. This crude product was then purified by column chromatography through silica gel, using a 1:1 by volume mixture of ethyl acetate and hexane as the eluent, to obtain the title compound in the form of two isomeric mixtures, which eluted separately from the column: (i) the first fraction consisting of 55 mg of a mixture of isomers having the (R,S)- and the (S,R)-configuration at the asymmetric carbon atoms marked respectively by *[1] and *[2] in formula (A), above, the mixture having an Rf=0.53 (thin layer chromatography on silica gel, using a 2:1 by volume mixture of ethyl acetate and hexane as the developing solvent); and (ii) the second fraction consisting of 50 mg of a mixture of isomers having the (R,R)- and the (S,S)-configuration at the asymmetric carbon atoms marked respectively by *[1] and *[2] in formula (A), above, the mixture having an Rf=0.41 (thin layer chromatography on silica gel, using a 2:1 by volume mixture of ethyl acetate and hexane as the developing solvent).

PREPARATION 1

5-(4-{2- [2-(2,5-Dimethoxy-3,4,6 -trimethylphenyl)-2-hydroxyethylamino]propoxy}benzyl)thiazolidine-2,4-dione A solution of 1.23 g of 2-amino-1-(2,5-dimethoxy-3,4,6-trimethylphenyl)ethanol [prepared as described in Preparation 14] and 3.0 g of 5-[4-(2-oxopropoxy)benzyl]-3-triphenylmethylthiazolidine-2,4-dione [prepared as described in Preparation 20] in 300 ml of benzene was heated under reflux for approximately 4 hours, during which time the water produced throughout the reaction was eliminated as a benzene azeotrope. The reaction mixture was then freed from benzene by distillation under reduced pressure. The residue was dissolved in a mixture of 100 ml of absolute methanol and 100 ml of absolute ethanol, after which 8.5 g of sodium borohydride were added to the solution. The resulting mixture was then heated under reflux for one hour. At the end of this time, the reaction mixture was freed from the alcohol by distillation under reduced pressure. The residue was then mixed with water and then it was extracted with ethyl acetate. The ethyl acetate layer was then washed twice with a saturated aqueous solution of sodium chloride, after which it was dried over anhydrous sodium sulfate. The solvent was then distilled off under reduced pressure, and 50 ml of trifluoroacetic acid were then added to the residue, whilst ice-cooling. The resulting mixture was then stirred at room temperature for one hour. At the end of this time, the trifluoroacetic acid was distilled off under reduced pressure and the residue was mixed with water. The aqueous mixture thus obtained was then neutralized with an aqueous solution of potassium carbonate, after which it was extracted with ethyl acetate. The extract was washed twice with a saturated aqueous solution of sodium chloride and then dried over anhydrous sodium sulfate. The solvent was removed by distillation under reduced pressure, after which the residue was purified by column chromatography through silica gel, using a 5:1 by volume mixture of ethyl acetate and ethanol as the eluent, to give 160 mg of the title compound, having an Rf=0.3 (thin layer chromatography on silica gel, using a 5:1 by volume mixture of ethyl acetate and ethanol as the developing solvent).

PREPARATION 2

5-{4-[2(R)-Aminopropoxy]benzyl}thiazolidine-2,4-dione trifluoroacetate (2a) 5-{4-[2(R)-t-Butoxycarbonylaminopropoxy]benzyl}-3-triphenylmethylthiazolidine-2,4-dione 13.2 g of diethyl azodicarboxylate were added dropwise to a solution of 20.7 g of triphenylphosphine in 300 ml of benzene, whilst ice-cooling. The mixture was then stirred at room temperature for 30 minutes, after which 35.0 g of 5-(4-hydroxybenzyl)-3-triphenylmethylthiazolidine-2,4-dione [prepared as described in Preparation 11] were added. The mixture was then stirred at room temperature for one hour, after which 13.2 g of (R)-2-t-butoxycarbonylamino-1-propanol were added to the mixture and the mixture was allowed to stand overnight at the same temperature. 40.9 g of triphenylphosphine, 23.68 ml of diethyl azodicarboxylate and 33 g of (R)-2-t-butoxycarbonylamino-1-propanol were then added, in turn and in 3 or 4 portions, to the mixture, and the mixture was stirred for 2 days. At the end of this time, the reaction mixture was freed from benzene by distillation under reduced pressure. The residue was then purified by column chromatography through silica gel, using a 1:3 by volume mixture of ethyl acetate and hexane as the eluent, to give 30.0 g of 5-{4-[2(R)-t-butoxycarbonylamino-1-propoxy]benzyl}-3-triphenylmethylthiazolidine-2,4-dione, melting at between 153° C. and 157° C.

$[\alpha]_D^{23} + 19.5°$ (c=1.000, chloroform).

(2b) 5-{4-[2(R)-Aminopropoxy]benzyl}thiazolidine-2,4-dione trifluoroacetate 500 ml of trifluoroacetic acid were added dropwise to a solution of 85.5 g of 5-{4-[2(R)-t-butoxycarbonylaminopropoxy]benzyl}-3-triphenylmethylthiazolidine-2,4-dione, [prepared as described in step (a), above] in 700 ml of methylene chloride, whilst ice-cooling, and the mixture was stirred at room temperature for 4 hours. At the end of this time, the reaction mixture was freed from methylene chloride and trifluoroacetic acid by distillation under reduced pressure. The residue was then triturated with a mixture of benzene and a small amount of ethyl acetate, and the crystals which precipitated were collected by filtration.

These crystals were recrystallized from a mixture of methanol and ethyl acetate to give 36.9 g of the title compound melting at between 162° C. and 166° C.

$[\alpha]_D^{23}$ −13.0° (c=0.885, methanol).

PREPARATION 3

5-{4-[2(R)-[2(R)-(3-Chlorophenyl)-2-t-butyldimethylsilyloxyethylamino]propoxy]benzyl}thiazolidine-2,4-dione A mixture of 36.5 g of 5-{4-[2(R)-aminopropoxy]benzyl}thiazolidine-2,4-dione trifluoroacetate [prepared as described in Preparation 2], 98.4 g of (R)-α-(t-butyldimethylsilyloxy)-α-(3-chlorophenyl)acetaldehyde [prepared as described in Preparation 12] and 400 ml of absolute methanol was stirred at room temperature for 2.5 hours, after which the mixture was cooled using a salted ice-bath. 29.0 g of sodium cyanoborohydride were then added to the mixture in small portions, and the mixture was allowed to stand overnight at room temperature. At the end of this time, the methanol was distilled off under reduced pressure, the residue was mixed with water and ethyl acetate, and the ethyl acetate layer was separated from the mixture. The ethyl acetate layer was then washed with a saturated aqueous solution of sodium chloride, after which it was dried over anhydrous sodium sulfate. The solvent was then distilled off under reduced pressure. The residue was purified by column chromatography through silica gel, using a 2:1 by volume mixture of ethyl acetate and hexane as the eluent, to give 46.5 g of the title compound.

$[\alpha]_D^{23}$ 26.3° (c=0.988, chloroform).

PREPARATION 4

5-(4-{2(R)-[2(R)-(3-Chlorophenyl)-2-hydroxyethylamino]propoxy}benzyl)thiazolidine-2,4-dione 88 g of tetrabutylammonium fluoride were added to a solution of 46.2 g of 5-(4-{2(R)-[2(R)-(3-chlorophenyl)-2-t-butyldimethylsilyloxyethylamino]propoxy}benzyl)-thiazolidine-2,4-dione [prepared as described in Preparation 3]in 500 ml of tetrahydrofuran, whilst ice-cooling, and the mixture was stirred at room temperature for 15 hours. At the end of this time, the tetrahydrofuran was distilled off under reduced pressure. The residue was then mixed with water and extracted with ethyl acetate. The extract was washed with a saturated aqueous solution of sodium chloride and dried over anhydrous sodium sulfate, after which the solvent was distilled off under reduced pressure. The residue was then purified by column chromatography through silica gel, using a 5:1 by volume mixture of ethyl acetate and ethanol as the eluent, to obtain the title compound in the form of crude crystals. These crystals were then recrystallized from a mixture of ethyl acetate and ethanol to give 27.1 g of the title compound melting at between 100° C. and 112° C.

$[\alpha]_D^{23}$ −4.4° (c=1.005, methanol).

PREPARATION 5

5-(4-{2-[2-(2-Naphthyl)-2-hydroxyethylamino]-propoxy}benzyl)thiazolidine-2,4-dione A procedure similar to that described in Preparation 10, below, was followed, but using 520 mg of 2-amino-1-(2-naphthyl)ethanol [prepared as described in Preparation 8], 650 mg of 5-[4-(2-oxopropoxy)benzyl]thiazolidine-2,4-dione [prepared as described in Preparation 9], 150 ml of benzene, 100 ml of absolute methanol and 1.25 g of sodium borohydride, to give the title compound in crude form. This crude product was then purified by column chromatography through silica gel, using a 5:1 by volume mixture of ethyl acetate and ethanol as the eluent, to give 490 mg of the title compound melting at between 115° C. and 145° C.

PREPARATION 6

5-(4-{2-[2-(3-Trifluoromethylphenyl)-2-hydroxyethylamino]propoxy}benzyl)thiazolidine-r 2,4-dione A procedure similar to that described in Preparation 10, below, was followed, but using 5.88 g of 2-amino-1-(3-trifluoromethylphenyl)ethanol [prepared as described in Preparation 13], 8 g of 5-[4-(2-oxopropoxy)-benzyl]-thiazolidine-2,4-dione [prepared as described in Preparation 9], 200 ml of benzene, 150 ml of absolute methanol and 5.4 g of sodium cyanoborohydride, to give the title compound in crude form. This crude product was then purified by column chromatography through silica gel, using ethyl acetate as the eluent, to give 4.05 g of the title compound melting at between 100° C. and 105° C.

PREPARATION 7

2-Amino-1-(3-chlorophenyl)ethanol 140 g of 3-chlorobenzaldehyde were added dropwise to a mixture of 112 g of trimethylsilylnitrile and 0.1 g of zinc iodide, and the resulting mixture was heated in an oil bath kept at 90° C. for 2.5 hours. At the end of this time, the reaction mixture was added dropwise to a mixture of 50 g of lithium aluminum hydride and 1200 ml of tetrahydrofuran, and the mixture was then heated under reflux for 40 minutes. The mixture was then cooled with ice, after which 50 ml of water, 50 ml of a 15% w/v aqueous solution of sodium hydroxide and 150 ml of water were added, in that order. Insoluble materials were filtered off, and the filtrate was concentrated by evaporation under reduced pressure. The concentrate was purified by column chromatography through silica gel, using a 10:4:1 by volume mixture of ethyl acetate, ethanol and triethylamine as the eluent, followed by distillation in vacuo, to give 66 g of the title compound as a liquid boiling at 140°–141° C./2.5 mmHg (333 Pa).

PREPARATION 8

2-Amino-1-(2-naphthyl)ethanol

A mixture of 7.4 g of 2-naphthaldehyde, 9.93 g of trimethylsilylnitrile and a catalytic amount of zinc iodide was heated in an oil bath kept at 90° C. for 2 hours. At the end of this time, the reaction mixture was added dropwise to a mixture of 5.7 g of lithium aluminum hydride and 500 ml of tetrahydrofuran, whilst ice-cooling, and the resulting mixture was then heated under reflux for 3 hours. 5.7 ml of water, 5.7 ml of a 15% w/v aqueous solution of sodium hydroxide and 17.1 ml of water were added dropwise, in that order, to the mixture. Insoluble materials were filtered off, and the filtrate was concentrated by evaporation under reduced pressure. The crystals obtained from the concentrate were recrystallized from a mixture of ethyl acetate and hexane, to give 7.21 g of the title compound as crystals, melting at between 113° C. and 116° C.

PREPARATION 9

5-[4-(2-Oxopropoxy)benzyl]thiazolidine-2,4-dione

9(a) 1-(4-Aminophenoxy)propan-2-one hydrochloride

A stream of hydrogen was passed through a mixture comprising 19.6 g of 1-(4-nitrophenoxy)propan-2-one, 300 ml of methanol, 30 ml of concentrated aqueous hydrochloric acid and 4 g of 10% w/v palladium-on-charcoal at room temperature for 5 hours. At the end of this time, the catalyst was filtered off, and the filtrate was concentrated by evaporation under reduced pressure, to give 20 g of the title compound. This compound was used directly and without further purification in the next step.

9(b) Ethyl 2-chloro-3-[4-(2-oxopropoxy)phenyl]propionate 50 ml of 35% w/v aqueous hydrochloric acid were added to a mixture of 20 g of 1-(4-aminophenoxy)propan-2-one hydrochloride [prepared as described in step (a) above], and 400 ml of acetone, and then a solution of 12 g of sodium nitrite in 20 ml of water was added dropwise to the resulting mixture, whilst ice-cooling; the mixture was then stirred at the same temperature for 20 minutes. At the end of this time, 130 g of ethyl acrylate and then 3.2 g of cuprous oxide were added in portions to the mixture, and the resulting mixture was stirred at room temperature for one hour. The reaction mixture was then concentrated by evaporation under reduced pressure, and the concentrate was mixed with water and ethyl acetate. The ethyl acetate layer was separated, washed with water and dried over anhydrous sodium sulfate; the solvent was then removed by distillation under reduced pressure. The resulting residue was purified by column chromatography through silica gel, using a 5:1 by volume mixture of hexane and ethyl acetate as the eluent, to give 11.3 g of the title compound having an Rf=0.31 (thin layer chromatography on silica gel, using a 5:1 by volume mixture of hexane and ethyl acetate as the developing solvent).

9(c) 5-[4-(2-Oxopropoxy)benzyl]thiazolidine-2,4-dione

A mixture comprising 12 g of ethyl 2-chloro-3-[4-(2-oxopropoxy)phenyl]propionate [prepared as described in step (b) above], 5 g of thiourea and 30 ml of sulfolane was heated at 90° C. for 3 hours, and then 100 ml of ethylene glycol monomethyl ether were added to the mixture, which was then heated for a further 4 hours. At the end of this time, 40 ml of water and 20 ml of concentrated aqueous hydrochloric acid were added to the reaction mixture, and the resulting mixture was heated for 4.5 hours in an oil bath kept at 100° C. After this, the reaction mixture was mixed with water and ethyl acetate, and then the ethyl acetate layer was separated, washed with water and dried over anhydrous sodium sulfate; the solvent was then removed by distillation under reduced pressure. The resulting residue was purified by column chromatography through silica gel, using a gradient elution method, with mixtures of hexane and ethyl acetate ranging from 3:2 to 2:3 by volume as the eluent, followed by crystallization from a mixture of ethyl acetate and hexane, to give 4.2 g of the title compound as crystals, melting at 158°–159° C.

PREPARATION 10

5-[4-{2-[2-(3-Chlorophenyl)-2-hydroxyethylamino]-propoxy}benzyl]thiazolidine-2,4-dione ½ ethyl acetate A solution of 2.5 g of 2-amino-1-(3-chlorophenyl)ethanol [prepared as described in Preparation 7] and 3.58 g of 5-[4-(2-oxopropoxy)benzyl]thiazolidine-2,4-dione [prepared as described in Preparation 9] in 50 ml of benzene was heated under reflux for 1.5 hours, whilst the water being formed during the reaction was continuously removed. At the end of this time, the benzene used was removed by distillation under reduced pressure. The resulting residue was dissolved in 100 ml of absolute methanol, and then 3 g of sodium borohydride were added to the resulting solution. The reaction mixture was allowed to stand overnight at room temperature, after which it was concentrated by evaporation under reduced pressure, and the concentrate was mixed with water. The resulting aqueous mixture was extracted with ethyl acetate, and the extract was dried over anhydrous sodium sulfate. The solvent was removed by distillation under reduced pressure, and the resulting residue was purified by column chromatography through silica gel, using ethyl acetate, followed by a 10:1 by volume mixture of ethyl acetate and ethanol, as the eluent. The product was recrystallized from ethyl acetate, to give 0.74 g of the title compound as crystals, melting at between 100° C. and 125° C.

PREPARATION 11

5-(4-Hydroxybenzyl)-3-triphenylmethylthiazolidine-2,4-dione

11(a) 5-(4-Acetoxybenzylidene)thiazolidine-2,4-dione

A mixture comprising 200 g of p-hydroxybenzaldehyde, 229 g of thiazolidine-2,4-dione, 280 g of sodium acetate and 660 ml of dimethylacetamide was stirred at 150° for one hour. It was then cooled, and 540 ml of dimethylacetamide and 370 ml of acetic anhydride were added to the reaction mixture. The resulting mixture was then stirred at 50° C. for 1.5 hours, after which it was poured into water. The solid which precipitated was collected by filtration, washed with water, and dried over anhydrous sodium sulfate, to give 390 g of the title compound, melting at between 238° C. and 240° C.

11(b) 5-(4-Acetoxybenzyl)thiazolidine-2,4-dione 2.0 g of 5-(4-acetoxybenzylidene)thiazolidine-2,4-dione [prepared as described in step (a) above] were dissolved in 80 ml of acetic acid and the mixture was hydrogenated by passing hydrogen at atmospheric pressure through the solution at 90° C. for 5 hours in the presence of 2.0 g of 10% w/w palladium-on-charcoal. At the end of this time, the catalyst was filtered off, and the filtrate was diluted with toluene. The acetic acid solvent was then removed by distillation as a toluene azeotrope. The crystals which separated out on adding toluene and hexane to the concentrate were collected by filtration and dried to give 1.8 g of the title compound, melting at between 115° C. and 117° C.

11(c) 5-(4-Acetoxybenzyl)-3-triphenylmethylthiazolidine-2,4-dione 3.43 g of triethylamine were added to a solution of 9.0 g of 5-(4-acetoxybenzyl)thiazolidine-2,4-dione [prepared as described in step (b) above] in 70 ml of methylene chloride, and a solution of 9.45 g of triphenylmethyl chloride in 30 ml of methylene chloride was added dropwise to the resulting mixture. The mixture was then stirred at room temperature for one hour, after which it was allowed to stand overnight at the same temperature. At the end of this time, the reaction mixture was mixed with water and ethyl acetate, and the organic layer was separated, washed with a saturated aqueous solution of sodium chloride, and dried over anhydrous sodium sulfate. The solvent was removed by distillation under reduced pressure, and the crystals which separated were washed with a mixture of hexane and ethyl acetate and dried, to give 7.86 g of the title compound, melting at between 152° C. and 156° C.

11(d) 5-(4-Hydroxybenzyl)-3-triphenylmethylthiazolidine-2,4-dione

A solution of 2.99 g of a 28% w/v methanolic solution of sodium methoxide in 10 ml of methanol was added dropwise, whilst ice-cooling, to a solution of 7.86 g of 5-(4-acetoxybenzyl)-3-triphenylmethylthiazolidine-2,4-dione [prepared as described in step (c) above] in 70 ml of toluene, and the resulting mixture was stirred at room temperature for one hour, after which it was allowed to stand overnight at the same temperature. The pH of the reaction mixture was then adjusted to a value of 4 by the addition of 1N aqueous hydrochloric acid, and the mixture was extracted with ethyl acetate. The extract was washed with water and dried over anhydrous sodium sulfate. The solvent was then removed by distillation under reduced pressure, and the crystals which appeared in the residue were collected, washed with hexane and dried, to give 6.0 g of the title compound, melting at between 158° C. and 160° C.

PREPARATION 12

(R)-α-t-Butyldimethylsilyloxy-α-(3-chlorophenyl) acetaldehyde

12(a) 3-Chloromandelic acid

A mixture of 158 g of 3-chlorobenzaldehyde, 111.6 g of trimethylsilylnitrile and a catalytic amount of zinc iodide was heated at 90° C. for 2 hours, with stirring. The reaction mixture was ice-cooled, and 350 ml of concentrated aqueous hydrochloric acid were added to it. The resulting mixture was then heated under reflux for one hour, after which it was mixed with water and with ethyl acetate. The ethyl acetate layer was separated and mixed with a 30% w/v aqueous solution of sodium hydroxide. The aqueous layer was separated, washed three times with ethyl acetate and then acidified with concentrated aqueous hydrochloric acid, after which it was extracted with ethyl acetate. The extract was washed with water and dried over anhydrous sodium sulfate. The solvent was then removed by distillation under reduced pressure, to give 172 g of the title compound as crystals, melting at between 110° C. and 114° C.

12(b) (R)-3-Chloromandelic acid and (S)-3-chloromandelic acid

A mixture of 100 g of 3-chloromandelic acid [prepared as described in Step (a), above] and 32.7 g of (R)-(+)-1-phenethylamine was dissolved in and recrystallized from a mixture of methanol and diethyl ether. The resulting crystals were collected by filtration, recrystallized three times from a mixture of methanol and diethyl ether and mixed with aqueous hydrochloric acid. The filtrate was used directly in the next step. The mixture was then extracted with ethyl acetate. The extract was dried over anhydrous sodium sulfate, and the solvent was removed by distillation under reduced pressure, to give 11.4 g of (R)-3-chloromandelic acid as crystals, melting at between 102° C. and 105° C.

$[\alpha]_D^{23}$ 153.7° (c=1.026, chloroform).

Hydrochloric acid was added to the filtrate obtained as described above, and the mixture was extracted with ethyl acetate. The extract was dried over anhydrous sodium sulfate, and the solvent was removed by distillation under reduced pressure. The resulting residue was mixed with 32.7 g of (S)-(−)-1-phenethylamine and was recrystallized three times from a mixture of methanol and diethyl ether, to give 11.2 g of (S)-3-chloromandelic acid as crystals, melting at between 101° C. and 104° C.

$[\alpha]_D^{23}$ +151.9° (c=1,008, chloroform).

12(c) Methyl (R)-3-chloromandelate 18.3 g of a 10% w/v solution of trimethylsilyldiazomethane in hexane were added dropwise to a solution of 28 g of (R)-3-chloromandelic acid [prepared as described in Step (b), above] in a mixture of 300 ml of methanol and 700 ml of benzene, and the resulting mixture was stirred for one hour. At the end of this time, the solvent was removed by distillation under reduced pressure, to give 28.6 g of the title compound having $[\alpha]_D^{23}$ −119.3° (c=1.00, chloroform) and an Rf=0.36 (thin layer chromatography on silica gel, using a 1:5 by volume mixture of ethyl acetate and hexane) as a crude product.

12(d) Methyl (R)-α-t-butyldimethylsilyloxy-3-chlorophenylacetate

A solution of 31.6 g of t-butyldimethylsilyl chloride in 200 ml of dimethylformamide was added dropwise, whilst ice-cooling, to a solution of 28 g of methyl (R)-3-chloromandelate [prepared as described in Step (c), above] and 28.5 g of imidazole in 300 ml of dimethylformamide, and the resulting mixture was stirred at the same temperature for 30 minutes, after which it was allowed to stand overnight at 40° C. At the end of this time, the reaction mixture was concentrated by evaporation under reduced pressure, and the residue was mixed with water and ethyl acetate. The ethyl acetate layer was separated and dried over anhydrous sodium sulfate, and then the solvent was removed by distillation under reduced pressure. The resulting residue was purified by column chromatography through silica gel, using a 1:15 by volume mixture of ethyl acetate and hexane as the eluent, to give 42.2 g of the title compound as crystals, melting at between 36° C. and 38° C.

$[\alpha]_D^{23}$ −39.1° (c=1.014, chloroform).

12(e) (R)-α-t-Butyldimethylsilyloxy-α-(3-chlorophenyl)acetaldehyde

A solution of 26 g of methyl (R)-α-t-butyldimethylsilyloxy-3-chlorophenylacetate [prepared as described in Step (d), above] in a mixture of 1000 ml of anhydrous hexane and 500 ml of dry toluene was cooled to −60° C., and then 124 ml of a 1M solution of diisobutylaluminum hydride in hexane were added dropwise to the cooled solution. The resulting mixture was stirred at the same temperature for 3 hours, after which 10 ml of water were added to it, and the temperature of the mixture was gradually allowed to rise to room temperature. The reaction mixture was then mixed with water and ethyl acetate, after which it was stirred for 30 minutes. Insoluble materials were filtered off using a Celite (trade mark) filter aid, and the ethyl acetate layer was separated from the filtrate and dried over anhydrous sodium sulfate. The ethyl acetate solvent was removed by distillation under reduced pressure, and the residue was purified by column chromatography through silica gel, using a 1:60 by volume mixture of ethyl acetate and hexane as the eluent, to give 5.41 g of the title compound having an Rf=0.36 (thin layer chromatography on silica gel, using a 1:60 by volume mixture of ethyl acetate and hexane as the developing solvent).

PREPARATION 13

2-Amino-1-(3-trifluoromethylphenyl)ethanol

Following a procedure similar to that described in Preparation 7, but using 25 g of 3-trifluoromethylbenzaldehyde, 15.71 g of trimethylsilylnitrile, a catalytic amount of zinc iodide, 12.8 g of lithium aluminum hydride and 400 ml of tetrahydrofuran, and then purifying the reaction product by column chromatography through silica gel, using a 2:1 by volume mixture of ethyl acetate and ethanol as the eluent, 25.2 g of the title compound were obtained as crystals, melting at 72° C. and having an Rf=0.25 (thin layer chromatography on silica gel, using a 10:3:1 by volume mixture of ethyl acetate, ethanol and triethylamine as the developing solvent).

PREPARATION 14

2-Amino-1-(2.5-dimethoxy-3,4,6-trimethylphenyl)ethanol

Following a procedure similar to that described in Preparation 7, but using 67 g of 2,5-dimethoxy-3,4,6-trimethylbenzaldehyde, 51 ml of trimethylsilylnitrile, 50 mg of zinc iodide, 36.63 g of lithium aluminum hydride and 2 l of tetrahydrofuran, and then purifying the reaction product by recrystallization from a mixture of ethyl acetate and hexane, 56.2 g of the title compound were obtained as crystals, melting at between 110° C. and 112° C.

PREPARATION 15

2(R)-t-Butoxycarbonylamino-4-methylpentanol 11.83 ml of triethylamine were added to a solution of 10 g of (R)-(—)-leucinol in 100 ml of dioxane and 50 ml of tetrahydrofuran, whilst ice-cooling. A solution of 18.6 g of di-t-butyl dicarbonate in 50 ml of tetrahydrofuran was then added dropwise to the reaction mixture. The resulting mixture was stirred at room temperature for 3 hours, after which the solvent was removed by distillation under reduced pressure to produce the title compound as a colorless oil, having an Rf=0.5 (thin layer chromatography on silica gel, using a 1:2 by volume mixture of ethyl acetate and hexane as the developing solvent).

PREPARATION 16

5-{4-[2(R)-t-Butoxycarbonylamino-4-methylpentyloxy]benzyl}-3-triphenylmethylthiazolidine-2,4-dione 2.1 g of 5-(4-hydroxybenzyl)-3-triphenylmethylthiazolidine-2,4-dione [prepared as described in Preparation 11] were added to a mixture of 2.28 g of 1,1'-azodicarbonyl-dipiperidine, 3.34 ml of tributylphosphine and 100 ml of anhydrous benzene. The resulting mixture was stirred at room temperature for one and a half hours, after which 2 g of 2(R)-t-butoxycarbonylamino-4-methylpentanol [prepared as described in Preparation 15] were added. The mixture was then stirred for a further five hours at the same temperature. At the end of this time, insolubles were filtered off and the filtrate was concentrated. The resulting residue was then purified by column chromatography through silica gel, using a 1:4 by volume mixture of ethyl acetate and hexane as the eluent, to obtain 1.05 g of the title compound, having an Rf=0.54 (thin layer chromatography on silica gel, using a 1:4 by volume mixture of ethyl acetate and hexane as the developing solvent).

PREPARATION 17

5-{4-[2(R)-Amino-4-methylpentyloxy]benzyl}thiazolidine-2,4-dione.trifluoroacetate A procedure similar to that described in Preparation 2, above, was followed, but using 1.03 g of 5-{4-[2(R)-t-butoxycarbonylamino-4-methylpentyloxy]benzyl}-3-triphenylmethylthiazolidine-2,4-dione [prepared as described in Preparation 16], 10 ml of methylene chloride and 10 ml of trifluoroacetic acid. After completion of the reaction, the methylene chloride and trifluoroacetic acid were removed by distillation under reduced pressure, and the residue was washed with toluene to give 640 mg of the title compound.

PREPARATION 18

5-(4-{2(R)-[2(R)-(3-Chlorophenyl)-2-t-butyldimethylsilyloxyethlamino]4-methylpentyloxy}benzyl)thiazolidine-2,4-dione A procedure similar to that described in Preparation 3, above, was followed, but using 540 mg of 5-{4-[2(R)-amino-4-methylpentyloxy]benzyl}thiazolidine-2,4-dione.trifluoroacetate [prepared as described in Preparation 17], 630 mg of (R)-α-(t-butyldimethylsilyloxy)-α-(3-chlorophenyl)acetaldehyde [prepared as described in Preparation 12], 614 mg of sodium cyanoborohydride and 10 ml of absolute methanol to give the title compound in crude form. This crude product was then purified by column chromatography through silica gel, using a 1:3 by volume mixture of ethyl acetate and hexane as the eluent, to give 420 mg of the title compound, having an Rf=0.70 (thin layer chromatography on silica gel, using a 1:1 by volume mixture of ethyl acetate and hexane as the developing solvent).

PREPARATION 19

5-(4-{2(R)-[2(R)-(3-Chlorophenyl)-2-hydroxyethylamino]-4-methylpentyloxy}benzyl)thiazolidine-2,4-dione A procedure similar to that described in Preparation 4, above, was followed, but using 350 mg of 5-(4-{2(R)-[2(R)-(3-chlorophenyl)-2-t-butyldimethylsilyloxyethylamino]-4-methylpentyloxy}benzyl]thiazolidine-2,4-dione [prepared as described in Preparation 18], 1,39 g of tetrabutyl ammonium fluoride and 10 ml of tetrahydrofuran to obtain the title compound in crude form. This crude product was then purified by column chromatography through silica gel, using a 1:1 by volume mixture of ethyl acetate and hexane as the eluent, to give 180 mg of the title compound, having an Rf=0.28 (thin layer chromatography on silica gel, using a 1:1 by volume mixture of ethyl acetate and hexane as the developing solvent).

PREPARATION 20

5-[4-(2-oxopropoxy)benzyl]-3-triphenylmethylthiazolidine-2,4-dione 9.2 g of 5-(4-hydroxybenzyl)-3-triphenylmethylthiazolidine [prepared as described in Preparation 11] were added to a solution of 2.3 g of potassium t-butoxide in 100 ml of tetrahydrofuran, whilst ice-cooling, and the mixture was stirred at room temperature until the compound added had dissolved. 4 g of bromoacetone were then added dropwise to the mixture in an ice bath, and the mixture was then allowed to stand at room temperature overnight. At the end of this time, 2.2 g of potassium t-butoxide and 10 g of bromoacetone were added to the reaction mixture, whilst ice-cooling. The resulting mixture was then stirred at room temperature for two hours, after which the reaction mixture was concentrated by evaporation under reduced pressure. A saturated aqueous solution of sodium chloride was then added thereto. The resulting mixture was extracted with ethyl acetate and then dried over anhydrous sodium sulfate. The ethyl acetate was then removed by evaporation under reduced pressure, and the resulting residue was purified by column chromatography through silica gel, using a 2:5 by volume mixture of ethyl acetate and hexane as the eluent, to obtain the title compound, having an Rf=0.46 (thin layer chromatography on silica gel, using a 1:2 by volume mixture of ethyl acetate and hexane as the developing solvent).

PREPARATION 21

2-Amino-1-(3,5-dimethyl-4-hydroxyphenyl)ethanol hydrochloride

21(a) 3,5-dimethyl-4-methoxymethoxybenzaldehyde

A solution of 9.0 g of 3,5-dimethyl-4-hydroxybenzaldehyde in 20 ml of dimethylformamide was added dropwise and whilst ice-cooling to a suspension of 3.14 g of a 55% w/w dispersion of sodium hydride in 50 ml of dimethylformamide. The mixture was then stirred for 20 minutes, after which 5.8 g of methyl chloromethyl ether were added, whilst ice-cooling. The resulting mixture was then stirred at room temperature for one hour. At the end of this time, water was added to the reaction mixture, and the mixture was extracted with ethyl acetate. The extract was then washed with a saturated aqueous solution of sodium chloride and dried over anhydrous sodium sulfate. The solvent was then removed by distillation under reduced pressure to give 11.0 g of the title compound.

21(b) 2-Amino-1-(3,5-dimethyl-4-methoxymethoxyphenyl)ethanol

A similar procedure to that described in Preparation 7, above, was followed, but using 11 g of 3,5-dimethyl-4-methoxymethoxybenzaldehyde [prepared as described in step (a), above], 14.05 g of trimethylsilyl nitrile, a catalytic amount of zinc iodide, 6.47 g of lithium aluminum hydride and 120 ml of tetrahydrofuran, to obtain 12.67 g of the title compound, melting at between 62° C. and 65° C.

21(c) 2-Amino-1-(3.5-dimethyl-4-hydroxyphenyl)ethanol hydrochloride

A solution of 10.55 g of 2-amino-1-(3,5-dimethyl-4-methoxymethoxyphenyl)ethanol [prepared as described in step (b), above] in 200 ml of a 4N solution of hydrogen chloride in dioxane was stirred at room temperature for 18 hours. The solvent was then removed by distillation under reduced pressure, to give 10.45 g of the title compound, melting at between 170° C. and 172° C.

PREPARATION 22

5-[4-{2-(2-[3,5-dimethyl-4-hydroxyphenyl]-2-hydroxyethylamino)propoxy}benzyl]thiazolidine-2,4-dione 1.93 g of a 28% w/w solution of sodium methylate in methanol was added to a solution of 2.18 g of 2-amino-1-(3,5-dimethyl-4-hydroxyphenyl)ethanol hydrochloride [prepared as described in Preparation 21] in 100 ml of ethanol, whilst ice-cooling. The solvent was then removed by distillation under reduced pressure and the mixture was concentrated to obtain a residue. A procedure similar to that described in Example 10, above, was then followed, using the 2-amino-1-(3,5-dimethyl-4-hydroxyphenyl)ethanol residue, obtained above, 2.8 g of 5-[4-(2-oxopropoxy)benzyl]thiazolidine-2,4-dione [prepared as desribed in Preparation 9], 50 ml of benzene, 2.5 g of sodium borohydride and 80 ml of absolute methanol, to obtain the title compound in crude form. This crude product was then purified by column chromatography through silica gel, using a 5:1 by volume mixture of ethyl acetate and ethanol as the eluent, to give 0.3 g of the title compound, having an Rf=0.48 (thin layer chromatography on silica gel, using a 4:1 by volume mixture of ethyl acetate and ethanol as the developing solvent).

We claim:

1. A compound of formula (I):

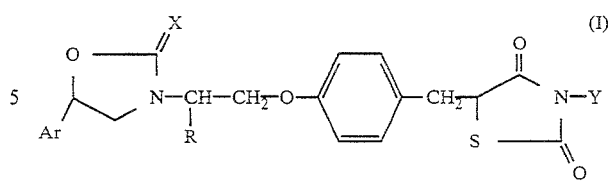

wherein:
R represents an alkyl group having from 1 to 8 carbon atoms;
X represents an oxygen atom or a sulfur atom;
Y represents a hydrogen atom or a group of formula —A—COOH, in which A represents an alkylene group having from 1 to 6 carbon atoms;
Ar represents an unsubstituted aryl group having from 6 to 10 ring carbon atoms or a substituted aryl group which has from 6 to 10 carbon atoms and which is substituted by at least one substituent selected from the group consisting of substituents A;

said substituents A are selected from the group consisting of: halogen atoms; haloalkyl groups, in which the alkyl part has from 1 to 4 carbon atoms; hydroxy groups; alkyl groups having from 1 to 4 carbon atoms; and alkoxy groups having from 1 to 4 carbon atoms;

and pharmaceutically acceptable salts and esters thereof.

2. The compound of claim 1, wherein Y represents a hydrogen atom or a group of formula —A—COOW, wherein A is as defined in claim 1 and W represents a hydrogen atom or an alkyl group having from 1 to 6 carbon atoms.

3. The compound of claim 1, wherein R represents an alkyl group having from 1 to 6 carbon atoms.

4. The compound of claim 1, wherein R represents an alkyl group having from 1 to 4 carbon atoms.

5. The compound of claim 1, wherein R represents a methyl or ethyl group.

6. The compound of claim 1, wherein A represents an alkylene group having from 1 to 4 carbon atoms.

7. The compound of claim 1, wherein A represents a methylene or ethylene group.

8. The compound of claim 1, wherein Ar represents an aryl group having from 6 to 10 ring carbon atoms, or an aryl group having from 6 to 10 ring carbon atoms substituted with from 1 to 5 subsituents, which may be the same or different, selected from the group consisting of substituents A, as defined in claim 1.

9. The compound of claim 1, wherein Ar represents an unsubstituted phenyl group, an unsubstituted naphthyl group or a phenyl or naphthyl group substituted with from 1 to 5 subsituents, which may be the same or different, selected from the group consisting of substituents A, as defined in claim 1.

10. The compound of claim 1, wherein Ar represents an unsubstituted phenyl group, an unsubstituted naphthyl group or a phenyl group substituted by from 1 to 5 substituents, which are the same or different, selected from the group consisting of substituents A';

said substituents A' are selected from the group consisting of: halogen atoms, trifluoromethyl groups, hydroxy groups, alkyl groups having from 1 to 4 carbon atoms and alkoxy groups having 1 or 2 carbon atoms.

11. The compound of claim 1, wherein Ar represents a phenyl, 2-chlorophenyl, 3-chlorophenyl 4-chlorophenyl, 3-bromophenyl, 3-fluorophenyl, 3-trifluoromethylphenyl, 3-methylphenyl, 3-methoxyphenyl, 3,5-dichlorophenyl, 3,5-di-t-butyl-4-hydroxyphenyl, 3,4,5-trimethoxyphenyl, 3-chloro-4-fluorophenyl, 2,5-dimethoxy-3,4,6-trimethylphenyl, 3,5-dimethyl-4-hydroxyphenyl or 2-naphthyl group.

12. The compound of claim 1, wherein:
R represents an alkyl group having from 1 to 6 carbon atoms;
X represents an oxygen atom or a sulfur atom;
Y represents a hydrogen atom or a group of formula —A—COOH, in which A represents an alkylene group having from 1 to 4 carbon atoms;
Ar represents an aryl group having from 6 to 10 ring carbon atoms, or an aryl group having from 6 to 10 ring carbon atoms substituted with from 1 to 5 substituents, which may be the same or different, selected from the group consisting of substituents A, as defined in claim 1; and
when Y represents the group of formula —A—COOH, the $C_1$ to $C_4$ alkyl esters thereof;
and pharmaceutically acceptable salts thereof.

13. The compound of claim 1, wherein:
R represents an alkyl group having 1 to 4 carbon atoms;
X represents an oxygen atom or a sulfur atom;
Y represents a hydrogen atom or a group of formula —A—COOH, in which A represents a methylene or an ethylene group; and
Ar represents an unsubstituted phenyl group, an unsubstituted naphthyl group or a phenyl or napthyl group substituted with from 1 to 5 substituents, which may be the same or different, selected from the group consisting of substituents A, as defined in claim 1; and
when Y represents a group of formula —A—COOH, the $C_1$ to $C_4$ alkyl esters thereof; and
pharmaceutically acceptable salts thereof.

14. The compound of claim 1, wherein:
R represents an alkyl group having 1 to 4 carbon atoms;
X represents an oxygen or sulfur atom;
Y represents a hydrogen atom or a group of formula: —$CH_2$—COOH;
Ar represents an unsubstituted phenyl group an unsubstituted naphthyl group or a phenyl group substituted by from 1 to 5 substituents which are the same or different, selected from the group consisting of substituents A';
said substituents A' are selected from the group consisting of: halogen atoms, trifluoromethyl groups, hydroxy groups, alkyl groups having from 1 to 4 carbon atoms and alkoxy groups having 1 or 2 carbon atoms; and
when Y represents the group of formula —$CH_2$—COOH, the $C_1$ to $C_4$ alkyl esters thereof; and
pharmaceutically acceptable salts thereof.

15. The compound of claim 1, wherein:
R represents a methyl or an ethyl group;
X represents an oxygen or sulfur atom;
Y represents a hydrogen atom or a group of formula: —$CH_2$—COOH;
Ar represents a group selected from the group consisting of: phenyl, 2-chlorophenyl, 3-chlorophenyl, 4-chlorophenyl, 3-bromophenyl, 3-fluorophenyl, 3-trifluoromethylphenyl, 3-methylphenyl, 3-methoxyphenyl, 3,5-dichlorophenyl, 3,5-di-t-butyl-4-hydroxyphenyl, 3,4,5-trimethoxyphenyl, 3-chloro-4-fluorophenyl, 2,5-dimethoxy-3,4,6-trimethylphenyl, 3,5-dimethyl-4-hydroxyphenyl and 2-naphthyl groups; and
when Y represents the group of formula —$CH_2$—COOH, the methyl and ethyl esters thereof;
and pharmaceutically acceptable salts thereof.

16. The compound of claim 1, selected from the group consisting of 3-{2-[4-(2,4-dioxothiazolidin-5-ylmethyl)phenoxy]-1-methylethyl}-5-(3-chlorophenyl)oxazolidin-2-one and pharmaceutically acceptable salts thereof.

17. The compound of claim 1, selected from the group consisting of 3-{2-[4-(3-methoxycarbonylmethyl-2,4-dioxothiazolidin-5-ylmethyl)phenoxy]-1-methylethyl}-5-(3-chlorophenyl)oxazolidin-2-one and pharmaceutically acceptable salts thereof.

18. The compound of claim 1, selected from the group consisting of 3-{2-[4-(2,4-dioxothiazolidin-5-ylmethyl)phenoxy]-1-methylethyl}-5-(3-chlorophenyl)oxazolidine-2-thione and pharmaceutically acceptable salts thereof.

19. The compound of claim 1, selected from the group consisting of 3-{2-[4-(3-methoxycarbonylmethyl-2,4-dioxothiazolidin-5-ylmethyl)phenoxy]-1-methylethyl}-5-(3-chlorophenyl)oxazolidine-2-thione and pharmaceutically acceptable salts thereof.

20. A pharmaceutical composition for the treatment or prophylaxis of diabetes, obesity, hyperlipemia, hyperglycemia, complications of diabetes, obesity-related hypertension and osteoporosis, which composition comprises an effective amount of an active compound in admixture with a pharmaceutically acceptable carrier or diluent, wherein the active compound is selected from the group consisting of compounds of formula (I):

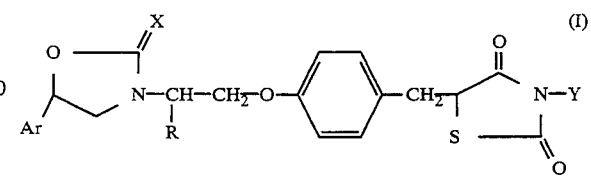

wherein:
R represents an alkyl group having from 1 to 8 carbon atoms;
X represents an oxygen atom or a sulfur atom;
Y represents a hydrogen atom or a group of formula —A—COOH, in which A represents an alkylene group having from 1 to 6 carbon atoms;
Ar represents an unsubstituted aryl group having from 6 to 10 ring carbon atoms or a substituted aryl group which has from 6 to 10 carbon atoms and which is substituted by at least one substituent selected from the group consisting of substituents A;
said substituents A are selected from the group consisting of: halogen atoms; haloalkyl groups, in which the alkyl part has from 1 to 4 carbon atoms; hydroxy groups; alkyl groups having from 1 to 4 carbon atoms; and alkoxy groups having from 1 to 4 carbon atoms;
and pharmaceutically acceptable salts and esters thereof.

21. The composition of claim 20, wherein:
R represents an alkyl group having from 1 to 6 carbon atoms;

X represents an oxygen atom or a sulfur atom;

Y represents a hydrogen atom or a group of formula —A—COOH, in which A represents an alkylene group having from 1 to 4 carbon atoms;

Ar represents an aryl group having from 6 to 10 ring carbon atoms, or an aryl group having from 6 to 10 ring carbon atoms substituted with from 1 to 5 substituents, which may be the same or different, selected from the group consisting of substituents A, as defined in claim 20; and when Y represents the group of formula —A—COOH, the $C_1$ to $C_4$ alkyl esters thereof;

and pharmaceutically acceptable salts thereof.

22. The composition of claim 20, wherein:

R represents an alkyl group having 1 to 4 carbon atoms;

X represents an oxygen atom or a sulfur atom;

Y represents a hydrogen atom or a group of formula —A—COOH, in which A represents a methylene or an ethylene group; and Ar represents an unsubstituted phenyl group, an unsubstituted naphthyl group or a phenyl or napthyl group substituted with from 1 to 5 substituents, which may be the same or different, selected from the group consisting of substituents A, as defined in claim 20; and when Y represents a group of formula —A—COOH, the $C_1$ to $C_4$ alkyl esters thereof; and pharmaceutically acceptable salts thereof.

23. The composition of claim 20, wherein:

R represents an alkyl group having 1 to 4 carbon atoms;

X represents an oxygen or sulfur atom;

Y represents a hydrogen atom or a group of formula: —$CH_2$—COOH;

Ar represents an unsubstituted phenyl group, an unsubstituted naphthyl group or a phenyl group substituted by from 1 to 5 substituents, which are the same or different, selected from the group consisting of substituents A';

said substituents A' are selected from the group consisting of: halogen atoms, trifluoromethyl groups, hydroxy groups, alkyl groups having from 1 to 4 carbon atoms and alkoxy groups having 1 or 2 carbon atoms; and when Y represents the group of formula —$CH_2$—COOH, the $C_1$ to $C_4$ alkyl esters thereof; and pharmaceutically acceptable salts thereof.

24. The composition of claim 20, wherein:

R represents a methyl or an ethyl group;

X represents an oxygen or sulfur atom;

Y represents a hydrogen atom or a group of formula: —$CH_2$—COOH;

Ar represents a group selected from the group consisting of: phenyl, 2-chlorophenyl, 3-chlorophenyl, 4-chlorophenyl, 3-bromophenyl, 3-fluorophenyl, 3-trifluoromethylphenyl, 3-methylphenyl, 3-methoxyphenyl, 3,5-dichlorophenyl, 3,5-di-t-butyl-4-hydroxyphenyl, 3,4,5-trimethoxyphenyl, 3-chloro-4-fluorophenyl, 2,5-dimethoxy-3,4,6-trimethylphenyl, 3,5-dimethyl-4-hydroxyphenyl and 2-naphthyl groups; and when Y represents the group of formula —$CH_2$—COOH, the methyl and ethyl esters thereof;

and pharmaceutically acceptable salts thereof.

25. The composition of claim 20, wherein said active agent is selected from the group consisting of:

3-{2-[4-(2,4-dioxothiazolidin-5-ylmethyl)phenoxy]-1-methylethyl}-5-(3-chlorophenyl)oxazolidin-2-one;

3-{2-[4-(3-methoxycarbonylmethyl-2,4-dioxothiazolidin-5-ylmethyl)phenoxy]-1-methylethyl}-5-(3-chlorophenyl)oxazolidin-2-one;

3-{2-[4-(2,4-dioxothiazolidin-5-ylmethyl)phenoxy]-1-methylethyl}-5-(3-chlorophenyl)oxazolidine-2-thione; and 3-{2-[4-(3-methoxycarbonylmethyl-2,4-dioxothiazolidin-5-ylmethyl)phenoxy]-1-methylethyl}-5-(3-chlorophenyl)oxazolidine-2-thione;

and pharmaceutically acceptable salts thereof.

26. A method for the treatment or prophylaxis of diabetes; obesity; hyperlipemia; hyperglycemia; complications of diabetes selected from the group consisting of retinopathy, nephropathy, neuropathy, cataracts, coronary heat disease, arteriosclerosis, obesity, hyperlipemia and hyperglycemia; obesity-related hypertension and osteoporosis in a mammal, which may be human, which method comprises administering to said mammal an effective amount of an active compound, wherein the active compound is selected from the group consisting of compounds of formula (I):

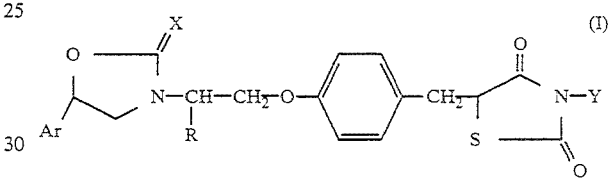

wherein:

R represents an alkyl group having from 1 to 8 carbon atoms;

X represents an oxygen atom or a sulfur atom;

Y represents a hydrogen atom or a group of formula —A—COOH, in which A represents an alkylene group having from 1 to 6 carbon atoms;

Ar represents an unsubstituted aryl group having from 6 to 10 ring carbon atoms or a substituted aryl group which has from 6 to 10 carbon atoms and which is substituted by at least one substituent selected from the group consisting of substituents A;

said substituents A are selected from the group consisting of: halogen atoms; haloalkyl groups, in which the alkyl part has from 1 to 4 carbon atoms; hydroxy groups; alkyl groups having from 1 to 4 carbon atoms; and alkoxy groups having from 1 to 4 carbon atoms;

and pharmaceutically acceptable salts and esters thereof.

27. The method of claim 26, wherein:

R represents an alkyl group having from 1 to 6 carbon atoms;

X represents an oxygen atom or a sulfur atom;

Y represents a hydrogen atom or a group of formula —A—COOH, in which A represents an alkylene group having from 1 to 4 carbon atoms;

Ar represents an aryl group having from 6 to 10 ring carbon atoms, or an aryl group having from 6 to 10 ring carbon atoms substituted with from 1 to 5 substituents, which may be the same or different, selected from the group consisting of substituents A, as defined in claim 26; and when Y represents the group of formula —A—COOH, the $C_1$ to $C_4$ alkyl esters thereof;

and pharmaceutically acceptable salts thereof.

28. The method of claim 26, wherein:
R represents an alkyl group having 1 to 4 carbon atoms;
X represents an oxygen atom or a sulfur atom;
Y represents a hydrogen atom or a group of formula —A—COOH, in which A represents a methylene or an ethylene group; and
Ar represents an unsubstituted phenyl group, an unsubstituted naphthyl group or a phenyl or napthyl group substituted with from 1 to 5 substituents, which may be the same or different, selected from the group consisting of substituents A, as defined in claim 26; and
when Y represents a group of formula —A—COOH, the $C_1$ to $C_4$ alkyl esters thereof; and
pharmaceutically acceptable salts thereof.

29. The method of claim 26, wherein:
R represents an alkyl group having 1 to 4 carbon atoms;
X represents an oxygen or sulfur atom;
Y represents a hydrogen atom or a group of formula: —CH$_2$—COOH;
Ar represents an unsubstituted phenyl group, an unsubstituted naphthyl group or a phenyl group substituted by from 1 to 5 substituents, which are the same or different, selected from the group consisting of substituents A';
said substituents A' are selected from the group consisting of: halogen atoms, trifluoromethyl groups, hydroxy groups, alkyl groups having from 1 to 4 carbon atoms and alkoxy groups having 1 or 2 carbon atoms; and
when Y represents the group of formula —CH$_2$—COOH, the $C_1$ to $C_4$ alkyl esters thereof; and
pharmaceutically acceptable salts thereof.

30. The method of claim 26, wherein:
R represents a methyl or an ethyl group;
X represents an oxygen or sulfur atom;
Y represents a hydrogen atom or a group of formula: —CH$_2$—COOH;
Ar represents a group selected from the group consisting of: phenyl, 2-chlorophenyl, 3-chlorophenyl, 4-chlorophenyl, 3-bromophenyl, 3-fluorophenyl, 3-trifluoromethylphenyl, 3-methylphenyl, 3-methoxyphenyl, 3,5-dichlorophenyl, 3,5-di-t-butyl-4-hydroxyphenyl, 3,4,5-trimethoxyphenyl, 3-chloro-4-fluorophenyl, 2,5-dimethoxy-3,4,6-trimethylphenyl, 3,5-dimethyl-4-hydroxyphenyl and 2-naphthyl groups: and
when Y represents the group of formula —CH$_2$—COOH, the methyl and ethyl esters thereof:
and pharmaceutically acceptable salts thereof.

31. The method of claim 26, wherein said active agent is selected from the group consisting of:
3-{2-[4-(2,4-dioxothiazolidin-5-ylmethyl)phenoxy]-1-methylethyl}-5-(3-chlorophenyl)oxazolidin-2-one;
3-{2-[4-(3-methoxycarbonylmethyl-2,4-dioxothiazolidin-5-ylmethyl)phenoxy]-1-methylethyl}-5-(3-chlorophenyl)oxazolidin-2-one:
3-{2-[4-(2,4-dioxothiazolidin-5-ylmethyl)phenoxy]-1-methylethyl}-5-(3-chlorophenyl)oxazolidine-2-thione: and
3-{2-[4-(3-methoxycarbonylmethyl -2,4-dioxothiazolidin-5-ylmethyl)phenoxy]-1-methylethyl}-5-(3-chlorophenyl)oxazolidine-2-thione:
and pharmaceutically acceptable salts thereof.

32. The method of claim 26 for the treatment or prophylaxis of diabetes.

33. The method of claim 26 for the treatment or prophylaxis of a complication of diabetes selected from the group consisting of retinopathy, nephropathy, neuropathy, cataracts, coronary heat disease and arteriosclerosis.

34. The method of claim 26 for the treatment or prophylaxis of a complication of diabetes selected from the group consisting of obesity, hyperlipemia and hyperglycemia.

* * * * *